(12) United States Patent
Powers

(10) Patent No.: US 9,107,817 B2
(45) Date of Patent: *Aug. 18, 2015

(54) METHOD OF PROMOTING MUCOSAL RECILIATION

(71) Applicant: Red Oax Holdings, LLC, Maitland, FL (US)

(72) Inventor: Kevin Powers, Maitland, FL (US)

(73) Assignee: Red Oax Holdings, LLC, Maitland, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/248,577

(22) Filed: Apr. 9, 2014

(65) Prior Publication Data

US 2014/0220156 A1 Aug. 7, 2014

Related U.S. Application Data

(62) Division of application No. 14/162,112, filed on Jan. 23, 2014, which is a division of application No. 13/460,426, filed on Apr. 30, 2012.

(60) Provisional application No. 61/480,764, filed on Apr. 29, 2011.

(51) Int. Cl.
| | |
|---|---|
| *A61K 9/00* | (2006.01) |
| *A61K 33/30* | (2006.01) |
| *A61K 33/00* | (2006.01) |
| *A61K 33/06* | (2006.01) |
| *A61K 33/14* | (2006.01) |
| *A61K 33/20* | (2006.01) |
| *A61K 33/24* | (2006.01) |

(52) U.S. Cl.
CPC ............... *A61K 9/0043* (2013.01); *A61K 33/00* (2013.01); *A61K 33/06* (2013.01); *A61K 33/14* (2013.01); *A61K 33/20* (2013.01); *A61K 33/24* (2013.01); *A61K 33/30* (2013.01)

(58) Field of Classification Search
None
See application file for complete search history.

(56) References Cited

U.S. PATENT DOCUMENTS

| | | | |
|---|---|---|---|
| 4,326,523 | A | 4/1982 | Wolfrom et al. |
| 4,581,226 | A * | 4/1986 | Dillon ............................ 424/49 |
| 4,600,711 | A | 7/1986 | Swerczek |
| 5,080,900 | A | 1/1992 | Stanley |
| 6,149,947 | A | 11/2000 | Hon et al. |
| 7,014,870 | B1 | 3/2006 | Hon et al. |
| 2002/0081726 | A1 | 6/2002 | Russell et al. |
| 2003/0013391 | A1 | 1/2003 | Nishihara |
| 2006/0105017 | A1 | 5/2006 | Walboomers et al. |
| 2007/0190178 | A1 | 8/2007 | Monroe et al. |
| 2007/0298121 | A1 | 12/2007 | Monroe et al. |
| 2008/0220091 | A1 | 9/2008 | Monroe et al. |

FOREIGN PATENT DOCUMENTS

WO 9411010 A2 5/1994

OTHER PUBLICATIONS

Huang et al., Mucosal healing and mucociliary transport change after endoscopic sinus surgery in children with chronic maxillary sinusitis. Int J Pediatr Otorhinolaryngol. 2006; vol. 70:1361-1367.
Kennedy DW, Pathogenesis of chronic rhinosinusitis. Ann Otol Rhinol Laryngol, 2004; Suppl. 193, vol. 113:6-9.
Gudis DA et al., Cilia dysfunction. Otolaryngol Clin North Am. 2010; vol. 43:461-472.
Kennedy et al., Functional endoscopic sinus surgery: Theory and diagnostic evaluation. Arch Otolaryngol. Sep. 1985; vol. 111:576-582.
Moriyama et al., Healing process of sinus mucosa after endoscopic sinus surgery. Am J Rhinol. 1996; vol. 10 (No. 2):61-66.
Shaw CK et al., A study of the normal temporal healing pattern and the mucociliary transport after endoscopic partial and full-thickness removal of nasal mucosa in sheep. Immunol Cell Biol. 2001; vol. 79:145-148.
Watelet JB et al., Wound healing of the nasal and paranasal mucosa: a review. Am J Rhinol. 2002; vol. 16 (No. 2):77-84.
Zahm JM et al., Wound repair of human surface respiratory epithelium. Am J Respir Cell Mol Biol. 1991; vol. 5:242-248.
Benali R et al., Tubule formation by human surface respiratory epithelial cells cultured in a three-dimensional collagen lattice. Am J Physiol. 1993; vol. 264:L183-L192.
Buisson AC et al., Gelatinase B is involved in the in vitro wound repair of human respiratory epithelium. J Cell Physiol. 1996; vol. 166:413-426.
Watelet JB et al., Neutrophil derived metalloproteinase-9 predicts healing quality after sinus surgery. Laryngoscope. Jan. 2005; vol. 115:56-61.
Proksch E et al. Bathing in a magnesium-rich Dead Sea salt solution improves skin barrier function, enhances skin hydration, and reduces inflammation in atopic dry skin. Int J Dermatol. 2005; vol. 44:151-157.

(Continued)

*Primary Examiner* — Sue Liu
*Assistant Examiner* — Thor Nielsen
(74) *Attorney, Agent, or Firm* — Michele L. Lawson; Smith & Hopen, P.A.

(57) ABSTRACT

The present invention relates to ionic compositions for promoting mucosal reciliation, particularly in the sinonasal cavity. The ionic components of the composition can include potassium, calcium, rubidium, zinc, bromide, and magnesium in an isotonic solution. In other embodiments, the ionic components of the composition can include magnesium, bromide, sulfate, sodium, and chloride.

19 Claims, 22 Drawing Sheets

(56) References Cited

OTHER PUBLICATIONS

Levi-Schaffer F et al., Inhibition of proliferation of psoriatic and healthy fibroblasts in cell culture by selected Dead-sea salts. Pharmacology. 1996; vol. 52:321-328.
Antunes MB et al. Murine nasal septa for respiratory epithelial air-liquid interface cultures. Biotechniques. Aug. 2007; vol. 43:195-204.
Schipor I et al., Quantification of ciliary beat frequency in sinonasal epithelial cells using differential interference contrast microscopy and high-speed digital video imaging. Am J Rhinol. 2006; vol. 20 (No. 1):124-127.
Chiu AG et al., Evaluation of the in vivo efficacy of topical tobramycin against *Pseudomonas* sinonasal biofilms. J Antimicrob Chemother. 2007; vol. 59:1130-1134.
Bleier BS et al., In vivo laser tissue welding in the rabbit maxillary sinus. Am J Rhinol. 2008; vol. 22: 625-628.
Bleier BS et al., Laser-assisted cerebrospinal fluid leak repair: an animal model to test feasibility. Otolaryngol Head Neck Surg. 2007; 137:810-814.
Tamashiro E et al., In vivo effects of citric acid/zwitterionic surfactant cleansing solution on rabbit sinus mucosa. Am J Rhinol Allergy. 2009; vol. 23 (No. 6):597-601.
Winters SL et al., Mechanosensitivity of mouse tracheal ciliary beat frequency: roles for Ca2+, purinergic signaling, tonicity, and viscosity. Am J Physiol Lung Cell Mol Physiol. 2007; 292:L614-L624.
Batts AH et al., The effect of some preservatives used in nasal preparations on mucociliary clearance. J Pharm Pharmacol. 1989; 41:156-159.
A. Pirayesh et al., The Efficacy of a Polyhydrated Ionogen Impregnated Dressing in the Treatment of Recalcitrant Diabetic Foot Ulcers: a Multi-centre Pilot Study, Acta chir belg, 2007, 107:675-681.
Depoortere D et al., Murine Ciliotoxicity and Rabbit Sinus Mucosal Healing by Polyhydrated Ionogen, Otolaryngology—Head and Neck Surgery, 2011, vol. 145 (No. 3):482-488.
Depoortere D et al. Enhanced post surgical remucosalization in a rabbit model. Otolaryngol Head Neck Surg. 2010; 143:p. 129.
Nayak, SR, Kirtane, MV, Ingle, MV, Functional Endoscopic Sinus Surgery—I (Anatomy, diagnosis, evaluation and technique). 1991 vol. 37, Issue 1, pp. 26-30.
Schleimer RP, Kato A, Kern R, et al. Epithelium: at the interface of innate and adaptive immune responses. J Allergy Clin Immunol. 2007; 120(6): 1279-1284.
Depoortere, MD, Jennifer M. Kofonow, MS, Bei Chen, MD, Alexander G. Chiu, MD, and Noam A. Chen, MD, PhD. Murine Ciliotoxicity and Rabbit Sinus Mucosal Healing by Polyhydrated Ionogen. American Academy of Otolaryngology—Head and Neck Surgery Foundation. Mar. 2011. pp. 1-7.
Depoortere, MD, Jennifer M. Kofonow, MS, Alexander G. Chiu, MD, Noam A. Cohen, MD, PhD, Polyhydrated Ionogen Enahnces postoperative sinonasal ciliated remucosalization. International Forum of Allergy & Phinology. Mar.-Apr. 2011 1(2):83-7.
Van Den Berg AJJ, Halkes SBA, Quarles Van Ufford HC, et al. A novel formulation of metal ions and citric acid reduces reactive oxygen species in vitro. J Wound Care. 2003; 12(10):413-418.
Pirayesh A, Dessy LA, Rogge FJ, et al. The efficacy of a polyhydrated ionogen impregnated dressing in the treatment of recalcitrant diabetic foot ulcers: a multi-centre pilot study. Acta Chir Belg. 2007;107:675-681.
Forsgren et al., Regeneration of Maxillary Sinus Mucosa Following Surgical Removal, Experimental Study in Rabbits, 1993, Ann Otol Rhinol Laryngol, vol. 102, pp. 459-466.
Zahm et al., Dynamics of Cell Movement During the Wound Repair of Human Surface Respiratory Epithelium, 1992, Biorhealogy, vol. 29, pp. 459-465.

\* cited by examiner

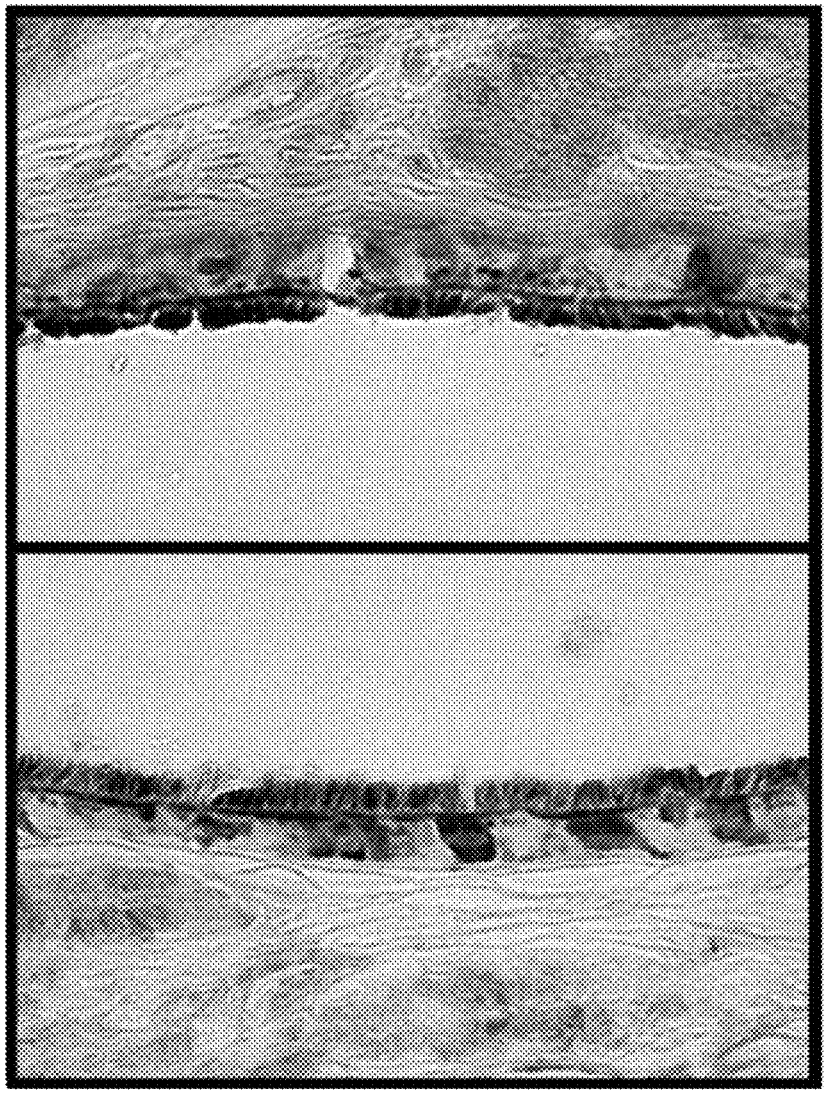

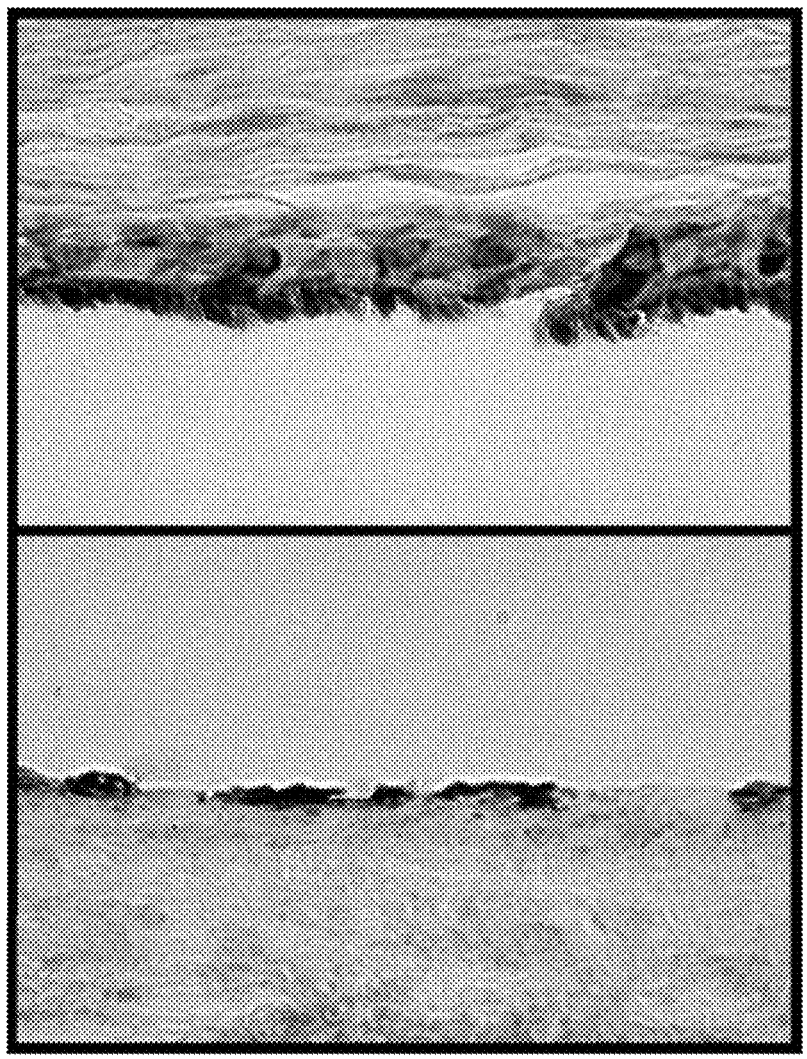

METHOD OF PROMOTING MUCOSAL RECILIATION

CROSS REFERENCE TO RELATED APPLICATIONS

This application is a divisional of and claims priority to currently pending U.S. Nonprovisional application Ser. No. 14/162,112, entitled "Methods of Enhancing Wound Healing", filed Jan. 23, 2014, which is a divisional of and claims priority to U.S. Nonprovisional application Ser. No. 13/460, 426, entitled "Compositions and Methods of Enhancing Wound Healing", filed Apr. 30, 2012, which claims priority to U.S. Provisional Application No. 61/480,764 entitled "Compositions and Methods of Enhancing Wound Healing", filed Apr. 29, 2011, the contents of each of which are hereby incorporated by reference into this disclosure.

FIELD OF INVENTION

This invention relates to promoting mucosal reciliation. Specifically, the invention provides compositions and methods to promote mucosal reciliation in epithelial mucosal tissue such as in the sinonasal region.

BACKGROUND OF INVENTION

Nasal Cavity

The nasal cavity is the body's first line of defense of the respiratory system that filters and removes airborne vapors, particles, pollutants, and toxins that are inhaled. The nasal passages are normally a self-cleaning structure that purifies and humidifies inhaled air prior to delivery of the vital gases to the lungs. Particles having about 5 um aerodynamic equivalent diameter (AED) or greater are normally removed by the nose and nasopharynx (about 85-90% are removed). Smaller particles may penetrate the lower respiratory tract to varying degrees.

The nasal passages are lined with a semi-permeable mucous membrane epithelium. The glands in each passage secrete protective fluids that keep the microbial flora in balance and protect against colonization and infection by overgrowth of surface microbes. The natural liquid products maintain a specific pH level to support the metabolic requirement of local host tissues while being unfavorable to the survival of microbes. In healthy individuals, the normal intranasal pH level of the mucous ranges from about 4 to about 7. The mucous generally is comprised of mucin of which about 2.5-3% is glycoprotein; about 1-2% is salts; and about 95% is water. Immunoglobulins comprise about 70% of the protein content.

Chronic Rhinosinusitis

Chronic rhinosinusitis is a common disorder that affects approximately 13% of the population in the United States. Chronic rhinosinusitis is an inflammatory disease of the mucosal lining of the sinuses and nasal cavity. Chronic rhinosinusitis symptoms include nasal congestion, facial pain, headache, nighttime coughing, an increase in previously minor or controlled asthma symptoms, general malaise, thick green or yellow discharge, feeling of facial fullness or tightness that may worsen when bending over, dizziness and aching teeth. A common treatment for chronic rhinosinusitis is functional endoscopic sinus surgery. In some cases, antibiotic treatment is also prescribed.

Wound Healing of the Nasal Mucosa

The sinonasal cavity is lined by pseudostratified columnar ciliated epithelium. The epithelium has a variable number of ciliated cells (~75%), goblet cells (~20%), and basal cells (~5%), which reside on an acellular basement membrane. This epithelial lining protects the upper airway from inhaled pathogens and debris by a process referred to as mucociliary clearance and contributes to the innate immunity and antigen presentation defense mechanisms. (Schleimer R P, Kato A, Kern R, et al. Epithelium: at the interface of innate and adaptive immune responses. *J Allergy Clin Immunol.* 2007; 120: 1279-1284). Performance is dependent on a complex interaction between motile cilia, glandular secretions and sinus anatomy. (Huang H M, Cheng J J, Liu C M, et al. Mucosal healing and mucociliary transport change after endoscopic sinus surgery in children with chronic maxillary sinusitis. *Int J Pediatr Otorhinolaryngol.* 2006; 70:1361-1367).

Chronic rhinosinusitis is a common disorder that affects approximately 13% of the population in the United States. Chronic rhinosinusitis results from inflammation of the sinonasal mucosa. Its symptoms include: nasal congestion; facial pain; headache; nighttime coughing; an increase in previously minor or controlled asthma symptoms; general malaise; thick green or yellow discharge; a feeling of facial fullness or tightness that may worsen when bending over; dizziness; and aching teeth. It should be stressed that the underlying etiology of the inflammation is multifactoral, with varying contributions from components of genetic predisposition as well as environmental exposures. (Kennedy D W. Pathogenesis of chronic rhinosinusitis. *Ann Otol Rhinol Laryngol Suppl.* 2004; 193:6-9.) However, invariable of the etiologic source, the common pathophysiologic endpoint is impaired mucociliary clearance with stagnant sinonasal secretions. (Gudis D A, Cohen N A. Cilia dysfunction. *Otolaryngol Clin North Am.* 2010; 43:461-472, vii).

Management of the disease is primarily focused on restoring mucociliary function and is typically accomplished with antimicrobial therapy (bacterial/fungal), anti-inflammatory therapy (topical or systemic steroids), and sinonasal lavage. While this combination approach is effective in a vast array of patients a subset of individuals require surgical intervention to relieve obstruction and restore mucociliary clearance.

Functional endoscopic sinus surgery (FESS) is a minimally invasive technique developed to restore the natural mucus clearance pathways. (Kennedy D W, Zinreich S J, Rosenbaum A E, et al. Functional endoscopic sinus surgery. Theory and diagnostic evaluation. *Arch Otolaryngol.* 1985; 111:576-582). As this technique has gained popularity, experience has demonstrated the importance of mucosal preservation; i.e., areas denuded of mucosa with exposed bone tend to develop osteitis with persistent inflammation. (Moriyama H, Yanagi K, Ohtori N, et al. Healing process of sinus mucosa after endoscopic sinus surgery. *Am J Rhinol.* 1996; 10:61-66). Additionally, these areas tend to demonstrate abnormal mucosal regeneration with inadequate mucociliary clearance. (Shaw C K, Cowin A, Wormald P J. A study of the normal temporal healing pattern and the mucociliary transport after endoscopic partial and full-thickness removal of nasal mucosa in sheep. *Immunol Cell Biol.* 2001; 79:145-148).

Uncertainty still exists concerning the sequence and time required for respiratory mucosa to heal. Differences in the extent and depth of trauma, animal species, and the criteria used to evaluate data may explain the disparate results reported. (Forsgren K, Stierna P, Kumlien J, et al. Regeneration of maxillary sinus mucosa following surgical removal. Experimental study in rabbits. Ann Otol Rhinol Laryngol. 1993; 102:459-466).

Wound healing is a highly organized process. Fibroblasts, leukocytes, and epithelial cells regulated by a wide variety of growth factors and cytokines interact resulting in inflammation, extracellular matrix (ECM) deposition and remodeling, cell migration, replication, and differentiation. A disturbance in this sequence can affect the normal function of the organ involved. (Watelet J B, Bachert C, Gevaert P, et al. Wound healing of the nasal and paranasal mucosa: a review. *Am J Rhinol.* 2002; 16:77-84). The process of wound repair has been extensively studied in other tissues such as the gingiva and the dermis, but epithelial wound repair in the nose and paranasal sinuses is still poorly understood. (Zahm J M, Chevillard M, Puchelle E. Wound repair of human surface respiratory epithelium. *Am J Respir Cell Mol Biol.* 1991; 5:242-248).

Injury to the nasal epithelium causes hemorrhage and exposes connective tissue. Subsequent vasoconstriction and platelet aggregation help control bleeding while fibrin and fibronectin, act as a provisional matrix for the influx of fibroblasts and monocytes. An intense inflammatory reaction is initiated simultaneously with the coagulation phase with neutrophils initially predominating. Three days after the injury the neutrophilic population is replaced by macrophages. (Watelet J B, Bachert C, Gevaert P, et al. Wound healing of the nasal and paranasal mucosa: a review. *Am J Rhinol.* 2002; 16:77-84).

Cell migration after wounding is an important process by which the respiratory epithelial barrier integrity is maintained. (Zahm J M, Pierrot D, Chevillard M, et al. Dynamics of cell movement during the wound repair of human surface respiratory epithelium. *Biorheology.* 1992; 29:459-465). The movement of respiratory cells from around the wound edge initiates within a few hours and is uniformly distributed. To initiate migration the apical-basal polarity of the cell is lost and cytoplasmatic extensions known as lamellipodia develop. (Watelet J B, Bachert C, Gevaert P, et al. Wound healing of the nasal and paranasal mucosa: a review. *Am J Rhinol.* 2002; 16:77-84). Small-size injuries may heal with no need for mitosis to occur, demonstrated by the use of colchicine, a mitosis inhibitor, which did not interrupt the repair process and cytochalasin B, an actin inhibitor, which prevented cell migration. (Zahm J M, Chevillard M, Puchelle E. Wound repair of human surface respiratory epithelium. *Am J Respir Cell Mol Biol.* 1991; 5:242-248). When replication is needed, undifferentiated basal cells from adjacent untraumatized areas are the main source of nascent cells. (Forsgren K, Stierna P, Kumlien J, et al. Regeneration of maxillary sinus mucosa following surgical removal. Experimental study in rabbits. *Ann Otol Rhinol Laryngol.* 1993; 102:459-466). Reorientation and differentiation follow while it appears that cilia require a reasonable base of epithelium before reciliation occurs and thus represent terminal differentiation. (Shaw C K, Cowin A, Wormald P J. A study of the normal temporal healing pattern and the mucociliary transport after endoscopic partial and full-thickness removal of nasal mucosa in sheep. *Immunol Cell Biol.* 2001; 79:145-148).

Postoperative outcomes from FESS are directly dependent on the healing quality of the nasal mucosa. (Watelet J B, Bachert C, Gevaert P, et al. Wound healing of the nasal and paranasal mucosa: a review. *Am J Rhinol.* 2002; 16:77-84). The ECM has a profound influence on cell adhesion and migration. Epithelial respiratory cells are able to retract collagen, transmitting contractile forces to the collagen fibrils. (Zahm J M, Pierrot D, Chevillard M, et al. Dynamics of cell movement during the wound repair of human surface respiratory epithelium. *Biorheology.* 1992; 29:459-465; Benali R, Tournier J M, Chevillard M, et al. Tubule formation by human surface respiratory epithelial cells cultured in a three-dimensional collagen lattice. *Am J Physiol.* 1993; 264:L183-L192).

Matrix Metalloproteinases (MMPs)

Matrix metalloproteinases (MMPs) are a family of secreted proteolytic enzymes that use ECM as a substrate and remodel the ECM which is a critical step in wound healing. It is now apparent that MMPs play an important role for many of the normal or pathological processes requiring matrix turnover. (Buisson A C, Zahm J M, Polette M, et al. Gelatinase B is involved in the in vitro wound repair of human respiratory epithelium. *J Cell Physiol.* 1996; 166:413-426).

Metalloproteinase-9 (MMP-9) expression is increased in the ECM and nasal fluids during wound healing, and is predominately derived from inflammatory cells, mainly neutrophils and macrophages. MMP-9 is known to actively degrade collagen, fibronectin, and elastin, subsequently interfering with the repair process. MMP-9 activity is controlled at multiple levels: transcriptional control by various cytokines, activation of the proenzyme by serine proteases or other metalloproteinases, and activity regulation by natural tissue inhibitors of metalloproteinases (TIMPs). It was reported that post-functional sinus surgery (post-FESS) patients with poor healing, characterized by edema, inflammation, and fibrosis, presented higher expression of MMP-9 in the ECM than those with good healing. (Watelet J B, Demetter P, Claeys C, et al. Neutrophil derived metalloproteinase-9 predicts healing quality after sinus surgery. *Laryngoscope.* 2005; 115:56-61).

Ions in Wound Healing

Various metal ions have been shown to be therapeutic in many diseases of man. For example, transition metal ions such as copper, iron, manganese and zinc serve as essential cofactors for a variety of biological processes including: cell energetics, gene regulation, and control of free radicals.

Potassium

Potassium, an electrolyte, is important for the proper function of all cells, tissues and organs in the human body. Potassium is necessary for proper heart function and plays a key role in skeletal and smooth muscle contraction, thus making it important for normal digestive and muscular function. Moderate to severe hypokalemia, or low plasma potassium levels, must often be redressed with oral potassium chloride supplementation or intravenous supplementation.

Magnesium

Magnesium is another ion that is necessary for more than 300 biochemical reactions in the body. Magnesium assists in maintaining normal muscle and nerve function; maintaining a steady heart rhythm; supporting a healthy immune system; maintaining strong bones; maintaining the normal functioning of enzymes; regulating blood sugar levels; regulating blood pressure; synthesizing proteins; maintaining the normal functioning of many hormones, particularly parathyroid hormone; and modulating energy metabolism. There is an increased interest in the role of magnesium in preventing and managing disorders such as hypertension, cardiovascular disease, and diabetes.

Changes in plasma magnesium levels usually affect the levels of other metal ions. For example, magnesium deficiency (hypomagnesemia) can cause low calcium and/or potassium levels. Symptoms of hypomagnesemia include muscle cramps and weakness, tremors, and abnormal heart rhythms. If the magnesium level is only a little low, the condition can be treated with oral magnesium tablets or by intramuscular injection. If the magnesium level is very low a large dose of magnesium can be given intravenously over a short time. Magnesium sulfate injections are also used to prevent premature contractions and to control seizures in pregnancy, to treat problems related to kidney conditions in children, and to treat heart attack and asthma patients.

Calcium

Calcium is another metal ion that is essential to maintaining total body health. Calcium is necessary for maintaining bones and teeth and ensuring proper functioning of muscles and nerves. Calcium deficiency can make the nervous system highly irritable causing tetany (spasms of the hands and feet, muscle cramps, abdominal cramps, and overly active reflexes). Chronic calcium deficiency contributes to poor mineralization of bones, soft bones (osteomalacia) and osteoporosis and, in children, rickets and impaired growth.

Calcium also plays a pivotal role in the physiology and biochemistry of the cell. For example, calcium acts as a second messenger in signal transduction pathways, in neurotransmitter release from neurons, contraction of all muscle cell types, and fertilization. Many enzymes require calcium ions as a cofactor, especially those of the blood-clotting cascade. Extracellular calcium is also important for maintaining the potential difference across excitable cell membranes.

Rubidium

Rubidium is a metal ion that is relatively safe with no known toxic effects. Rubidium has been used in therapy for chronic mental conditions in humans such as depression. It has a mild tranquilizing effect, and can be administered to those with nervous disorders and epilepsy. Rubidium is chemically similar to potassium and cesium, and is one of the few compounds available that is capable of entering cancer cells. Due to this ability and its pH, it is used in high pH cancer therapies. Some studies have shown that rubidium therapy can shrink tumors, by replacing the potassium that allows the cells to replicate. Rubidium has also been shown to regulate cell membranes; regulate insulin levels; aid in digestion of proteins; aid in the release of hormones from the pituitary gland; control release of fluids from the salivary glands; and aid in regulating heartbeat. A lack of rubidium can cause depression, dehydration of the cells, susceptibility to cancer, hair loss, and decreased tolerance to glucose.

Zinc

Zinc is one of the essential trace elements in humans and is ubiquitous in subcellular metabolism. It is an essential component of at least one catalytic site of at least one enzyme in every enzyme classification. Altogether, several hundred zinc metalloenzymes have been identified in the plant and animal kingdoms, including matrix metalloproteins that are important in wound healing.

Wound healing solutions containing cations, such as polyhydrated ionogen solution (PHI), were originally based on constituents found in red oak tree bark which was used as a traditional wound dressing of the Native American Indians. The original cation containing solutions were based on a combination of citric acid and metallic ions such as potassium, calcium, rubidium and zinc. The formulation is aimed at modulating extracellular protease activity, altering reactive oxygen species and modulating expression of inflammatory cytokines (Monroe S, Sampson E M, Popp M P. Effect of Polyhydrated Ionogen (PHI) on Viability and Matrix Metalloproteinase Levels in Cultures of Normal and Diabetic Human Dermal Fibroblasts. Chicago, Ill.: Wound Healing Society; 2005; van den Berg A J J, Halkes S B A, Quarles van Ufford H C, et al. A novel formulation of metal ions and citric acid reduces reactive oxygen species in vitro. Wound Care. 2003; 12:413-418). The formulation has been demonstrated to improve healing in chronic wounds such as diabetic foot ulcers. (Pirayesh A, Dessy L A, Rogge F J, et al. The efficacy of a polyhydrated ionogen impregnated dressing in the treatment of recalcitrant diabetic foot ulcers: a multicentre pilot study. *Acta Chir Belg.* 2007; 107:675-681).

The use of MgBr2 for dermatologic issues such as psoriasis dates back to the ancient Egyptians and has demonstrated inhibitory effects on fibroblast outgrowth. (Proksch E, Nissen H P, Bremgartner M, et al. Bathing in a magnesium-rich Dead Sea salt solution improves skin barrier function, enhances skin hydration, and reduces inflammation in atopic dry skin. Int J Dermatol. 2005; 44:151-157; Levi-Schaffer F, Shani J, Politi Y, et al Inhibition of proliferation of psoriatic and healthy fibroblasts in cell culture by selected Dead-sea salts. Pharmacology. 1996; 52:321-328).

Given the difficulty in successfully healing wounds in the mucosa of the nasal cavity, what is needed is a composition that enhances wound healing and promotes recilialization in the mucosa.

SUMMARY OF THE INVENTION

The present application determined that the therapeutic potential of a cation containing formulation realized in dermatologic wounds could be translated to sinonasal mucosal healing. A novel combination of metal ions that is safe and exhibits unanticipated additive/synergistic effects in the efficacy of treatment of inflamed and injured mucosal tissue and sinuses is presented. The combination of ions such as potassium (K+), rubidium (Rb+), magnesium, (Mg2+), calcium (Ca2+), zinc (Zn2+), and bromide (Br−) with a pharmaceutically acceptable carrier in an isotonic solution provides for enhanced healing of damaged mucosal tissue over the treatment of this form of injury by any one of the metal ions alone and relative to the current standard of care by normal saline solution (buffered or unbuffered). An effective amount of citrate and/or citric acid as well as sulfate may also be added to the solution of the present invention. Water may be the pharmaceutically acceptable carrier. This solution may be administered at least once per day in an amount from between about 0.1 ounces to about 30 ounces per day.

A method of enhanced wound healing is presented in which an isotonic solution containing an effective amount of $K^+$, $Rb^+$, $Ca^{2+}$, $Zn^{2+}$, $Mg^{2+}$, $SO_4^{2-}$ and $Br^-$ ions is administered to a subject at least once per day. Citric acid or citrate may also be added to the composition. This enhanced wound healing may be sinonasal mucosal healing and the solution may be administered via a nasal spray. The amount administered can be from between about 0.1 ounces to about 30 ounces per day.

A method of promoting mucosal reciliation is also presented in which an isotonic solution containing an effective amount of $K^+$, $Rb^+$, $Ca^{2+}$, $Zn^{2+}$, $Mg^{2+}$, $SO_4^{2-}$ and $Br^-$ ions is administered to a subject at least once per day. Citric acid or citrate may also be added to the composition. In an alternative embodiment, a method of promoting mucosal reciliation is presented in which an isotonic solution containing an effective amount of magnesium ($Mg^{2+}$), bromide ($Br^-$), sodium ($Na^+$), chloride ($Cl^-$), and sulfate ($SO_4^{2-}$) without the preservative potassium sorbate is administered to a subject at least once per day. The amount administered can be from between about 0.1 oz. to about 30 oz.

A method of debriding tissue is presented in which an isotonic solution containing an effective amount of $K^+$, $Rb^+$, $Ca^{2+}$, $Zn^{2+}$, $Mg^{2+}$, $SO_4^{2-}$ and $Br^-$ ions is administered to a subject at least once per day. Citric acid or citrate may also be added to the composition. The amount administered can be from between about 0.1 ounces to about 30 ounces per day.

In addition, an isotonic solution containing magnesium ($Mg^{2+}$), bromide ($Br^-$), sodium ($Na^+$), chloride ($Cl^-$), and sulfate ($SO_4^{2-}$) without the preservative potassium sorbate is also capable of promoting enhanced healing of injured mucosal tissue when administered at least once per day in an amount from between about 0.1 ounces to about 30 ounces per day.

In an alternative embodiment, a method of enhancing wound healing is presented in which an isotonic solution containing an effective mount of magnesium ($Mg^{2+}$), bromide ($Br^-$), sodium ($Na^+$), chloride ($Cl^-$), and sulfate ($SO_4^{2-}$) without the preservative potassium sorbate is administered to a subject at least once per day. The amount administered can be from between about 0.1 ounces to about 30 ounces per day. This enhanced wound healing may be sinonasal mucosal healing and the solution may be administered via a nasal spray.

BRIEF DESCRIPTION OF THE DRAWINGS

FIG. 8 is a series of images from the uninjured lateral wall that are Type IV β-tubulin-stained. (A) a maxillary sinus treated with saline and (B) a maxillary sinus treated with a sterile isotonic formulation of $K^+$, $Rb^+$, $Ca^{2+}$, $Zn^{2+}$ (Solution 2) without the preservative potassium sorbate.

FIG. 9 is a series of images from the injured upper medial wall that are Type IV β-tubulin-stained. (A) a maxillary sinus treated with saline and (B) a maxillary sinus treated with a sterile isotonic formulation of $K^+$, $Rb^+$, $Ca^{2+}$, $Zn^{2+}$ (solution 2) without the preservative potassium sorbate. As shown in (B), daily treatment with the isotonic formulation of $K^+$, $Rb^+$, $Ca^{2+}$, $Zn^{2+}$ (Solution 2) without the preservative potassium sorbate has resulted in recilialization.

DETAILED DESCRIPTION OF THE PREFERRED EMBODIMENT

Figure 1A:
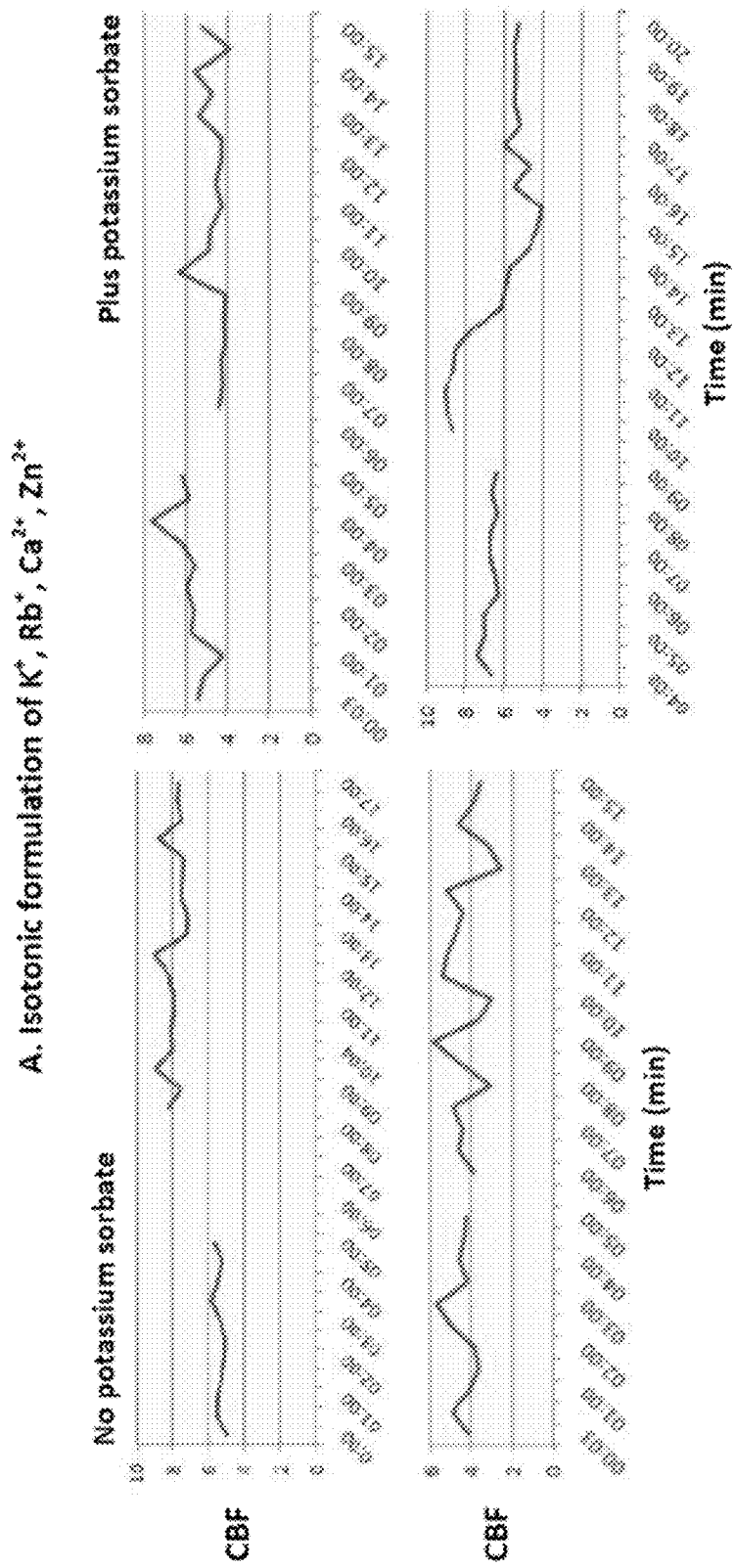
FIG. 1 is a series of images depicting the effect of three various metal ion formulations on mouse cilial function. (A) isotonic formulation of $K^+$, $Rb^+$, $Ca^{2+}$ and $Zn^{2+}$ (Solution 2) with and without the preservative potassium sorbate; (B) isotonic formulation of $K^+$, $Rb^+$, $Ca^{2+}$, $Zn^{2+}$, $Mg^{2+}$ and $Br^-$ (Solution 3) with and without the preservative potassium sorbate; (C) hypertonic formulation of $K^+$, $Rb^+$, $Ca^{2+}$, $Zn^{2+}$, $Mg^{2+}$ and $Br^-$ (Solution 1 plus $Mg^{2+}$ and $Br^-$) with and without the preservative potassium sorbate.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

DEFINITIONS

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the hundredth of the unit unless specifically specified otherwise. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "about" as used herein is not intended to limit the scope of the invention but instead encompass the specified material, parameter or step as well as those that do not materially affect the basic and novel characteristics of the invention. The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "composition" as used herein describes an agent, compound, chemical, or extract that can be administered or tested by the present invention as promoting wound healing in a subject. The chemical can be of any composition such as inorganic, organic, or a biomolecule. A biomolecule can be a molecule of any biological origin that can be found in or produced by, at least in part, a cell and is meant to include ions such as the metal ions of the present invention. "Composition" is used interchangeably herein with "solution", "compound", "agent", "chemical", "ingredient" and "extract".

The term "ion" as used herein describes a molecule, a portion of a molecule (e.g. Zwitterion), cluster of molecules, molecular complex, moiety or atom in which the total number of electrons is not equal to the total number of protons thus giving it a net positive (cation) or a negative (anion) electronic charge. Alternatively, the molecule may not contain a net positive or negative charge but can be made to contain a net positive or negative charge. Both cations and anions are included in the term "ion". Ions of the present invention may be produced by dissolving salts, including but not limited to, potassium citrate; magnesium chloride; rubidium chloride; calcium chloride; zinc chloride; magnesium bromide; and magnesium sulfate. Cations useful in the present invention include, but are not limited to, potassium, magnesium, rubidium, calcium, and zinc. Anions useful in the present invention include, but are not limited to, citrate, chloride, bromide, and sulfate.

The term "counterion" as used herein describes an ion that accompanies an ionic species in order to maintain electric neutrality in the composition. For example, the counterion of the sodium cation may be the chloride anion and vice versa.

The term "Solution 1" or "original solution" as used herein refers to a sterile hypertonic formulation containing $K^+$, $Rb^+$, $Ca^{2+}$, and $Zn^{2+}$ with or without the preservative potassium sorbate.

The term "Solution 2" as used herein refers to a sterile isotonic formulation containing $K^+$, $Rb^+$, $Ca^{2+}$, and $Zn^{2+}$ without the preservative potassium sorbate.

The term "Solution 3" as used herein refers to a sterile isotonic formulation containing $K^+$, $Rb^+$, $Ca^{2+}$, $Zn^{2+}$, $Mg^{2+}$, $SO_4^{2-}$, and $Br^-$ without the preservative potassium sorbate.

The term "Solution 4" as used herein refers to a sterile isotonic formulation containing $Mg^{2+}$, $Br^-$, Na+, Cl-, and $SO_4^{2-}$ without the preservative potassium sorbate.

"Subject" is used to describe an animal, preferably a human, to whom treatment is administered, including prophylactic treatment with the compositions of the present invention. "Subject" and "patient" are used interchangeably herein.

The term "therapeutically effective amount" as used herein is defined as concentrations or amounts of components which are sufficient to effect beneficial or desired clinical results, including, but not limited to, promoting wound healing; promoting debridement of tissue after surgery; reducing reactive oxygen species; modulating protease binding; modulating matrix metalloproteinase levels; promoting cilial regeneration, particularly in mucosal membranes; enhancing interaction with enzymes involved in biosynthetic pathways necessary for wound healing; reducing the level of superoxide anions associated with the wound; modulating human complement activation; reducing scar tissue; reducing inflammation; upregulating growth factors; reducing cytokines; and decreasing bacteria in the wound. Compositions of the present invention can be used to effect a favorable change in the condition whether that change is an improvement or a complete elimination of a wound. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The effective amount of the compositions of the present invention encompasses providing enhanced wound healing without causing significant side effects or adverse reactions. The terms "therapeutically effective amount", "therapeutically effective dose", "effective amount", and "effective dose" are used interchangeably herein.

The term "ameliorates" as used herein refers to a change in state from a first to a second state, where the first state is the condition of the epithelium prior to the application of the composition, and the second state is the condition of the epithelium after application of the composition where the condition of the second state is improved as compared to the first state as a result of the application of the composition.

The term "ciliated epithelium" or "ciliated tissue" as used herein refers to all ciliated epithelial structures including, but not limited to, nasal mucosa, sinus and paranasal sinus, trachea and middle ear.

The term "matrix metalloproteinase" or "MMP" as used herein refers to proteases which are zinc-dependent endopeptidases that are capable of degrading extracellular matrix proteins as well as process a number of bioactive molecules. During wound repair, different MMPs can be produced by multiple cell types. For example, MMP-2 is only produced by inflammatory cells while MMP-9 is produced by keratinocytes as well as inflammatory cells. MMPs are not normally actively expressed in uninjured skin either in the epidermis or dermis. Reducing MMP levels in wounds can assist in enhancing wound healing.

The term "administrating" or "administration" as used herein are defined as the process by which the compositions of the present invention are delivered to the individual for treatment or prevention purposes. The composition can be delivered nasally, orally, rectally, percutaneously, intravaginally, topically, intraocularly, intrauterinely, or by injection in dosage unit formulations containing conventional nontoxic pharmaceutically acceptable carriers, adjuvants, and vehicles as desired. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. For injection compositions, the carrier will usually comprise sterile water, at least in large part, though other ingredients, for example, to aid solubility, may be included. Injectable solutions, for example, may be prepared in which the carrier comprises saline solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, or a spot-on treatment.

In some embodiments, the interval between each administration is constant. The administration of the composition may be spaced at time intervals such as at about every 24 hours; at about every 23 hours; at about every 22 hours; at about every 21 hours; at about every 20 hours; at about every 19 hours; at about every 18 hours; at about every 17 hours; at about every 16 hours; at about every 15 hours; at about every 14 hours; at about every 13 hours; at about every 12 hours; at about every 10 hours; at about every 9 hours; at about every 8 hours; at about every 7 hours; at about every 6 hours; at about every 5 hours; at about every 4 hours; at about every 3 hours; at about every 2 hours; or at about every 1 hour. Administration can also be continuous and adjusted to maintaining a level of the compound within any desired and specified range.

The amount of ions in the composition will depend on absorption, distribution, metabolism, and excretion rates as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compositions used in the present invention. The amount of ions in the solution is presented as the concentration in percent (w/v). This is equivalent to the mg of the particular ion per 100 mL of working solution.

The dose of the compounds administered to a subject may vary with the particular composition, the method of administration, and the particular disorder being treated. The dose should be sufficient to affect a desirable response, such as a therapeutic or prophylactic response against a particular disorder or condition. For example, the dosage of a compound of the invention administered in the form of a nasal spray can be about 0.1 oz. (equivalent to about 3 ml or 3 cc) to about 30 oz. (equivalent to about 882.2 ml or cc), including all units in between, when the composition is administered at least once per day. It is contemplated that one of ordinary skill in the art can determine and administer the appropriate dosage of compounds disclosed in the current invention according to the foregoing considerations.

The administration of the composition can be extended over an extended period of time, such as from about a day or shorter up to about a year or longer. For example, the dosing regimen can be extended over a period of any of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and 31 days or over a period of any of about 1, 2, 3, 4, 5, 6, 7, 8, 9, 10, 11, 12, 15, 18, 21 or 24 months or over a period of 1, 2, 3, 4, 5 or longer years. In an embodiment, the composition may be administered for about 14 days. In another embodiment, the composition may be administered for at least 14 days. In a further embodiment, the composition may be administered for between about 14 days and about 30 days. In some embodiments, there is no break in the dosing schedule. In some embodiments, the interval between each administration is no more than about 24 hours.

The compounds used in the present invention may be administered individually, or in combination with or concurrently with one or more other compounds known to enhance wound healing. Additionally, compounds used in the present invention may be administered in combination with or concurrently with other therapeutics for debridement of necrotic or damaged tissue; therapeutics for reducing reactive oxygen species; therapeutics for modulating protease binding; and therapeutics for modulating matrix metalloproteinase levels.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, nontoxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, saline, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

The preparation process of the composition is designed to maintain the maximum therapeutic effect of the composition and method. The parameters of the composition are controlled such as its isotonicity, pH range, and temperature. For example, the pH of the solution of the present invention may be slightly acidic to limit any potential stinging upon use and to encourage protease inhibition since protease inhibition is maximized at an acidic pH. The term "slightly acidic" refers to a pH that ranges from about 5 to about 6.9. The composition of the present invention may be an isotonic solution or a hypertonic solution. Tonicity for the solution may be between about 0.9% and about 4%. In a beneficial embodiment, the solution is isotonic or slightly hypertonic.

The present invention can be applied to enhance wound healing, both internally and externally. Administration of the composition of the present invention provides an improvement in wound healing for all types of epithelium and mucosa including, but not limited to, the respiratory system including, but not limited to, the throat, trachea, lungs, nasal cavity, sinuses, and larynx; the middle ear; the gastrointestinal system including, but not limited to the esophagus, the stomach, and the small and large intestines; the reproductive system including, but not limited to the vagina, cervix, uterus, fallopian tubes and ovaries; the dermis; and the eyes.

While the present invention can be applied to both internal and external wound healing as well as to tissue health in general, it will be described in connection with chronic rhinosinusitis, maxillary mucosal injury, and sinonasal inflammation in particular. The description with relation to chronic rhinosinusitis is used as an example and is not to be construed as limiting as the process of the present invention includes treatment of any mucosal tissue. In a representative embodiment, the mucosal membranes of the nasal passages are treated with a novel, specifically formulated mineral cationic solution that cleanses, debrides, soothes and heals inflamed and injured sinonasal ciliated mucosa.

In the chronic rhinosinusitis example, the solution may be applied to the nasal passages and paranasal sinuses by a number of forms including, but not limited to, nasal drops; nasal sprays; nasal mists; nasal rinse; nebulizers; creams; and gels.

The solution of the present invention can be buffered with a weak acid including, but not limited to, citric acid, acetic acid, lactic acid and gluconic acid in a pH range between about 5.0 to about 7.0 including all units in between. In an embodiment, the pH range can be between about 6.0 to about 6.8. In a further embodiment, the pH can be about 6.5. Citrate ($C_6H_8O_7^{3-}$) may be used to adjust the pH in some embodiments.

In an embodiment, the solution can include citric acid ($C_6H_8O_7$) in the range of about 0.01-0.1% (w/v), including all units in between to the hundredth of a percent. In an embodiment, the range may be between about 0.018-0.082% (w/v) including all units in between to the thousandth of a percent. In a further embodiment, the concentration may be about 0.03% (w/v). In a further embodiment, the concentration may be about 0.03654% (w/v). The pH of the final solution can be adjusted by the addition of a base including, but not limited to, ammonia, carbonates and hydroxides of barium, calcium, cesium, lithium, potassium, rubidium, sodium, and strontium. In a beneficial embodiment, the base is potassium hydroxide (KOH).

A listing of potential ions as well as ranges of concentrations that can be used in Solutions 1-4 are given below. The type and percentage of ion used varies between the solutions. Not all ions are present in all solutions. The cations may be obtained using different salts other than those listed below. These alternative salts may have different hydration states or use different counterions. Examples of salts that may be used include, but are not limited to, citrate, chloride, bromide, sulfate, bicarbonate, lactate, and phosphate. One of ordinary skill in the art would recognize the alternative salts that may be used in conjunction with the present invention.

Potassium citrate, typically $K_3$citrate.$H_2O$, is present in the composition such that the potassium concentration [$K^+$] is in the range of about 0.02-3.0% (w/v), including all units in between to the hundredth of a percent. In an embodiment, the range may be between about 0.2056-1.2336% (w/v) including all units in between to the ten thousandth of a percent. In a further embodiment, the concentration may be about 0.4% (w/v). In a further embodiment, the concentration may be about 0.4112% (w/v). The citrate concentration [$C_6H_5O_7^{3-}$] can be in the range of about 0.03-4.7% (w/v), including all units in between to the hundredth of a percent. In an embodiment, the range may be between about 0.33145-1.9887% (w/v) including all units in between to the hundred thousandth of a percent. In a further embodiment, the concentration may be about 0.6% (w/v). In a further embodiment, the concentration may be about 0.6629% (w/v).

Magnesium chloride, typically $MgCl_2.6H_2O$, is present in the composition such that the magnesium concentration [$Mg^{2+}$] is in the range of about 0.007-1.14% (w/v), including all units in between to the thousandth of a percent. In an embodiment, the range may be between about 0.072-0.43182% (w/v), including all units in between to the hundred thousandth of a percent. In a further embodiment, the concentration may be about 0.14% (w/v). In a further embodiment, the concentration may be about 0.14394% (w/v). The chloride [$Cl^-$] concentration can be in the range of about 0.001-2.3% (w/v) including all units in between to the thousandth of a percent. In an embodiment, the range may be between about 0.21-1.255% (w/v) including all units in between to the thousandth of a percent. In a further embodiment, the concentration may be about 0.41% (w/v). In a further embodiment, the concentration may be about 0.41832% (w/v).

Rubidium chloride, typically RbCl, is present in the composition such that the rubidium concentration [$Rb^+$] is in the range of about 0.0001-4.0% (w/v), including all units in between to the ten thousandth of a percent. The lower end of this range may be 0 in cases where rubidium is not present in the solution. In an embodiment, the range may be between about 0.0015-0.0095% (w/v) including all units in between to the ten thousandth of a percent. In a further embodiment, the concentration may be about 0.003% (w/v). In a further embodiment, the concentration may be about 0.0031453% (w/v).

Calcium chloride, typically $CaCl_2.2H_2O$, is present in the composition such that the calcium concentration [$Ca^{2+}$] is in the range of about 0.000005-1.3% (w/v), including all units in between to the millionth of a percent. The lower end of this range may be 0 in cases where calcium is not present in the solution. In an embodiment, the range may be between about 0.000057-0.00034284% (w/v) including all units in between to the millionth of a percent. In a further embodiment, the concentration may be about 0.00011428% (w/v).

Zinc chloride, typically $ZnCl_2$, is present in the composition such that the zinc concentration [$Zn^{2+}$] is in the range of about 0.0000057-2.12% (w/v), including all units in between to the millionth of a percent. The lower end of this range may be 0 in cases where zinc is not present in the solution. In an embodiment, the range may be between about 0.000012-0.0000741% (w/v). In a further embodiment, the concentration may be about 0.0000247% (w/v).

Magnesium bromide, typically $MgBr_2.6H_2O$, is present in the composition such that the bromide concentration [$Br^-$] is in the range of about 0.0002-0.2.6% (w/v), including all units in between to the ten thousandth of a percent. The lower end of this range may be 0 in cases where bromide is not present in the solution. In an embodiment, the range may be between about 0.0022-0.01335516% (w/v). In a further embodiment, the concentration may be about 0.00445172% (w/v).

Magnesium sulfate, typically $MgSO^4.7H_2O$, is present in the composition such that the sulfate concentration [$SO_4^{2-}$] is in the range of about 0.000078-4.5% (w/v), including all units in between to the millionth of a percent. The lower end of this range may be 0 in cases where sulfate is not present in the solution. In an embodiment, the range may be between about 0.00077-0.004677% (w/v) including all units in between to the millionth of a percent. In a further embodiment, the concentration may be about 0.001559% (w/v).

Sodium chloride, typically NaCl, is present in the composition such that the sodium concentration [$Na^+$] is in the range of about 0.005%-3.0% (w/v) including all units in between to the thousandth of a percent. The lower end of this range may be 0 in cases where sodium is not present in the solution. In one embodiment, [$Na^+$] is in the range of about 0.05%-0.4833% (w/v) including all units in between to the ten thousandth of a percent. In a further embodiment, the concentration may be about 0.16% (w/v). In another embodiment, [$Na^+$] concentration is about 0.1610936% (w/v).

Before use, the final solution can be sterilized using any one of a number of methods, including, but not limited to, heating at 80° C. for 2 hours, sterile filtering through an about 0.2 m filter, gamma irradiation, or any other appropriate method known to those skilled in the art.

Various counterions may be used in the solutions of the present invention including, but not limited to, citrate, chloride, bromide, sulfate, hydroxide, bicarbonate, carbonate, phosphate, lactate, glutamate, and acetate as well as other anions that are found in physiological systems. In some embodiments, non-physiological anions such as bromide can be used.

The mineral salt constituents of the solutions can include, but are not limited to: potassium citrate, magnesium chloride, rubidium chloride, calcium chloride, zinc chloride, magnesium bromide, magnesium sulfate, and sodium chloride. A pharmaceutically acceptable carrier including, but not limited to, water and/or aqueous solutions of water and hydrophilic polymers such as polyethylene glycol and methyl cellulose are added to each solution to act as a debrider and moisturizer.

The composition can contain additional inactive ingredients including, but not limited to, preservatives such as potassium sorbate, benzoic acid, chlorhexidine acetate and/or gluconate, parabens and potassium sorbate as well as emulsifying agents and stabilizers such as glycerol monosterate and methylcellulose, respectively.

The composition of the present invention can be administered in a variety of ways to a subject as described above. For example, in sinonasal administration the easiest route of administration is through a liquid in the form of a nasal spray, nasal drops, or nasal mist. If administered by nasal spray, about 0.1 oz. to about 30 oz. may be administered to the subject at least once per day. In a beneficial embodiment, the nasal spray is administered about twice per day. As a non-limiting example, the nasal spray may be administered in a dosage of 8 ounces, twice a day, with 4 ounces being administered into each nostril twice a day. The nasal spray may be administered between about 1 day and about 14 days or longer. In a beneficial embodiment, the nasal spray is administered for about 14 days.

Specific Solution Formulations

Solution 2 (sterile isotonic formulation containing $K^+$, $Rb^+$, $Ca^{2+}$, and $Zn^{2+}$ without the preservative potassium sorbate), may contain from between about 0.02-3.0% (w/v) of $K^+$; from between about 0.0001-4.0% (w/v) of $Rb^+$; from between about 0.000005-1.3% (w/v) of $Ca^{2+}$; and from between about 0.0000057-2.12% (w/v) of $Zn^{2+}$. A beneficial amount of $K^+$ is about 0.924% (w/v). A beneficial amount of $Rb^+$ is about 0.007068% (w/v). A beneficial amount of $Ca^{2+}$ is about 0.0002568% (w/v). A beneficial amount of $Zn^{2+}$ is about 0.0000554% (w/v). Solution 2 may also contain citrate ($C_6H_5O_7^{3-}$) in a range from between about 0.03-4.7% (w/v). A beneficial amount of $C_6H_5O_7^{3-}$ is about 1.57% (w/v). Solution 2 may also contain citric acid ($C_6H_5O_7$) in a range from between about 0.01-0.1% (w/v). If chloride salts are used, Cl– can be present in about 0.0034464% (w/v) in a beneficial embodiment. In one beneficial embodiment, Solution 2 may be administered at least once per day.

Solution 3 (sterile isotonic formulation containing $K^+$, $Rb^+$, $Ca^{2+}$, $Zn^{2+}$, $Mg^{2+}$, and $Br^-$ without the preservative potassium sorbate), may contain from between about 0.02-3.0% (w/v) of $K^+$; from between about 0.0001-4.0% (w/v) of $Rb^+$; from between about 0.000005-1.3% (w/v) of $Ca^{2+}$; from between about 0.0000057-2.12% (w/v) of $Zn^{2+}$; from about 0.007-1.14% (w/v) of $Mg^{2+}$; and from about 0.0002-2.6% (w/v) of $Br^-$. A beneficial amount of $K^+$ is about 0.4112% (w/v). A beneficial amount of $Rb^+$ is about 0.0031453% (w/v). A beneficial amount of $Ca^{2+}$ is about 0.00011428% (w/v). A beneficial amount of $Zn^{2+}$ is about 0.0000247% (w/v). A beneficial amount of $Mg^{2+}$ is about 0.14394% (w/v). A beneficial amount of $Br^-$ is about 0.00445172% (w/v). Solution 3 may also contain citrate ($C_6H_5O_7^{3-}$) in a range from between about 0.03-4.7% (w/v) and sulfate ($SO_4^{2-}$) in a range from about 0.000078-4.5% (w/v). A beneficial amount of $C_6H_5O_7^{3-}$ is about 0.6629% (w/v). A beneficial amount of $SO_4^{2-}$ is about 0.001559% (w/v). Solution 3 may also contain citric acid ($C_6H_5O_7$) in a range from between about 0.01-0.1% (w/v). If chloride salts are used, Cl– can be present in about 0.41832% (w/v) in a beneficial embodiment. The amount of Cl– can be adjusted to correspond to the concentration of other ions present in the solution to ensure that a tonicity of between about 0.9% and about 3.5% is maintained in the solution. In one beneficial embodiment, Solution 3 may be administered at least once per day.

In one beneficial embodiment of Solution 3, the following salts and concentrations may be used in preparing 10 L of solution: potassium citrate at a concentration of about 1.13728% (w/v); magnesium chloride at a concentration of about 1.195% (w/v); rubidium chloride at a concentration of about 0.00445% (w/v); calcium chloride at a concentration of about 0.0004192% (w/v); zinc chloride at a concentration of about 0.0000514% (w/v); magnesium bromide at a concentration of about 0.00814% (w/v); magnesium sulfate at a concentration of about 0.004% (w/v); and citric acid at a concentration of about 0.03654% (w/v). Water is added to the solution and the pH is preferably adjusted to about 6.5. Less than about 2.4% (w/v) of the salts are contained in the solution. The amounts disclosed are the amounts that can be present in one 6 oz. (equivalent to about 177.44 ml) bottle of solution.

Solution 4 (sterile isotonic formulation containing $Mg^{2+}$, $Br^-$, $SO_4^{2-}$, $Na^+$, and Cl– without the preservative potassium sorbate), may contain from between about 0.007-1.14% (w/v) of $Mg^{2+}$; from between about 0.0002-2.6% (w/v) of $Br^-$; from between about 0.000078-4.5% (w/v) of $SO_4^{2-}$; from between about 0.005-3.0% (w/v) of $Na^+$; and from between about 0.001-2.3% (w/v) of Cl–. A beneficial amount of $Mg^{2+}$ is about 0.14394% (w/v). A beneficial amount of $Br^-$ is about 0.00445172% (w/v). A beneficial amount of $SO_4^{2-}$ is about 0.001559% (w/v). A beneficial amount of $Na^+$ is about 0.1610936% (w/v). A beneficial amount of Cl– is about 0.6652122% (w/v). In one beneficial embodiment, Solution 4 may be administered at least once per day.

In an embodiment of Solution 4, the amounts of salts and concentrations of salts can be obtained similarly to the formulation of Solution 3 by using the concentration of ions disclosed above for Solution 4 and adjusting for the presence of the corresponding salt.

The solutions of the present invention are preferably prepared in batches of at least 10 L due to the small amount needed of some of the ingredients as well as for convenience. All ingredients are used below their solubility limits and thus they are all readily soluble in the aqueous medium of the solution. Constant stirring is generally needed during preparing the solutions. While the ingredients may be added in any order, it may be preferable to add the ingredients that are present in larger quantities first in order to aid in the mixing process. Some ingredients may need to be prepared in dilute "pre-solutions" due to considerations of accurate weighing of the lesser amounts of ingredients.

Preliminary Studies on Biocompatibility and Safety of the Present Invention

Cytotoxicity

Following the requirements of International Organization for Standardization (ISO 10993-5): Biological Evaluation of Medical Devices—Part 5: Tests for Cytotoxicity, In Vitro Methods, the present invention showed no evidence of causing any cell lysis or toxicity. L-929 mouse fibroblast cells were seeded in 10 $cm_2$ wells and incubated at 37° C. in the presence of 5% $CO_2$ to obtain subconfluent monolayers of cells. When the cells had grown to subconfluency, the growth medium was removed from over them and replaced with 2 mL of 2% agarose in 2×MEM (Minimal Essential Medium supplemented with 10% fetal bovine serum, 4% antibiotics (200 units/mL penicillin, 200 g/mL streptomycin, and 5.0 g/mL amphotericin) and 2% (4 mM) L-glutamine) and neutral red. The agarose mixture was allowed to solidify over the cells to form an agarose overlay. The agarose over the cells was covered with four articles in triplicate as follows:

1) 0.1 mL sodium chloride (0.9%) on a filter disc as a negative control
2) A 1 cm length of HDPE as a negative control
3) A 1 cm×1 cm portion of latex as a positive control
4) 0.1 mL present invention on a filter disc These articles were incubated on the cells at 37° C. in the presence of 5% $CO_2$ for 24 hours. After incubation, the cells were examined macroscopically for cell decolorization around the test article and controls to determine the zone of cell lysis (if any). After macroscopic examination, the cell monolayers were examined microscopically (100×) to verify any decolorized zones and to determine cell morphology in proximity to the article. Scoring for cytotoxicity was based on the following criteria in Table 1 below:

TABLE 1

| Grade | Reactivity | Condition of Cultures |
| --- | --- | --- |
| 0 | None | No detectable zone around or under specimen |
| 1 | Slight | Some malformed or degenerated cells under specimen |
| 2 | Mild | Zone limited to area under specimen |
| 3 | Moderate | Zone extending specimen size up to 1.0 cm |
| 4 | Severe | Zone extending farther than 1.0 cm beyond specimen |

For the suitability of the system to be confirmed, the negative control must have been a grade of 0 (reactivity none) and the positive control must have been a grade equal to or greater then a grade of 3 (reactivity moderate to severe). The test article containing the preferred embodiment of the present invention passed the test if all three monolayers were less than or equal to a grade of 2 (reactivity mild). The scores obtained were as shown in Table 2 below:

TABLE 2

| Articles | | Zone of Lysis | Grade | Reactivity |
|---|---|---|---|---|
| Test article filter discs | (1) | 0 | 0 | None |
| containing extract of | (2) | 0 | 0 | None |
| the present invention | (3) | 0 | 0 | None |
| Filter disc containing | (1) | 0 | 0 | None |
| 0.9% normal saline | (2) | 0 | 0 | None |
| | (3) | 0 | 0 | None |
| Negative Control: | (1) | 0 | 0 | None |
| 1 cm length of HDPE | (2) | 0 | 0 | None |
| | (3) | 0 | 0 | None |
| Positive Control: | (1)* | 7 | 3 | Moderate |
| 1 cm × 1 cm portion | (2)* | 7 | 3 | Moderate |
| of latex | (3)* | 8 | 3 | Moderate |

*Complete cell lysis was beneath the sample

Conclusion: The present invention showed no evidence of causing any cell lysis or toxicity. The safety of the present invention was confirmed in the second biocompatibility test as follows:

Intracutaneous Reactivity

Following the requirements of International Organization for Standardization (ISO 10993-10): Biological Evaluation of Medical Devices—Part 10: Tests for Irritation and Delayed-Type Hypersensitivity (modified for a chemical solution), the present invention showed no erythema and no edema when injected intracutaneously into rabbits.

Two male New Zealand White rabbits were used for the study. Fur was clipped off the back of both animals over an area just large enough for the injections, and 0.2 mL dose of Solution 3 (test article) was injected by the intracutaneous route into five separate sites on the right side of the back of each animal. Similarly, 0.2 mL of 0.9% sodium chloride (USP solution) was injected into five sites on the left side of the back of each animal as a negative control. Injections were placed approximately 2 cm apart. The appearance of each injection site was noted immediately after injection and at 24, 48, and 72 hours after injection. Any reactions were scored on a 0 to 4 basis and any reactions at the injection site were also noted.

The reactions were evaluated according to the subjective rating scale depicted in Table 3 below:

TABLE 3

| Score | Erythema | Edema |
|---|---|---|
| 0 | No erythema | No edema |
| 1 | Very slight erythema (barely perceptible) | Very slight edema (barely perceptible) |
| 2 | Well-defined erythema | Well-defined edema (edges of area Well-defined by definite rising) |
| 3 | Moderate erythema | Moderate edema (raised approximately 1 mm) |
| 4 | Severe erythema (beet redness) to eschar Formation preventing grading of erythema | Severe edema (raised more than 1 mm, and Extending beyond exposure area) |

The mean erythema and edema scores for both the control and test article sites in each animal at each scoring interval were calculated as follows: All mean erythema and edema scores for the test and control articles were totaled and divided by 12 (2 animals×3 grading periods×2 grading categories) to determine to overall mean scores for each article. The difference between to overall mean score of the control article subtracted from the overall mean score of the test article was determined. If the overall mean score of the test article was less than the overall mean score of the control article, 0.0 was reported. The requirements of the test were met if the difference between the overall test article mean score and overall control article mean score was 1.0 or less. Both animals appeared normal throughout the study and the results of all scores are shown in Table 4 below:

TABLE 4

| | | | Scoring Interval | | | | | | | | | | |
|---|---|---|---|---|---|---|---|---|---|---|---|---|---|
| | | Body | 24 hours | | | | 48 hours | | | | 72 hours | | | |
| | | Weight | Test | | Control | | Test | | Control | | Test | | Control | |
| Animal Number | Sex | (kg) | ER | ED | ER | ED | ER | ED | ER | ED | ER | ED | ER | ED |
| 69695 | Male | 2.4 | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| Mean Score | | | 0.0 | 0.0 | 0.0 | 0.0 | 0.0 | 0.0 | 0.0 | 0.0 | 0.0 | 0.0 | 0.0 | 0.0 |
| 69698 | Male | 2.4 | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| | | | 0 | 0 | 0 | 0 | 0 | 0 | 0 | 0 | 0 | 0 | 0 | 0 |
| Mean Score | | | 0.0 | 0.0 | 0.0 | 0.0 | 0.0 | 0.0 | 0.0 | 0.0 | 0.0 | 0.0 | 0.0 | 0.0 |

Conclusion: The present invention injected intracutaneously into rabbits resulted in no erythema and no edema.

Systemic Toxicity

The Systemic Toxicity Test was performed in accordance with the requirements of International Organization for Standardization (ISO 10993-11): Biological Evaluation of Medical Devices—Part 11: Tests for Systemic Toxicity (modified to increase the observation period from 72 hours to 5 days and to dose a solution instead of an extract), and based on the United States Pharmacopeia, National Formulary, General Chapter <88>, Biological Reactivity Tests, In Vitro. The study was conducted in accordance with the provisions of the FDA Good Laboratory Practice (GLP) Regulations (21 CFR, Part 58) evaluating Solution 3 (test article) for acute systemic toxicity in mice. Following the injection of a single 25 mL/kg dose via the intraperitoneal route into mice, Solution 3 showed no mortality or evidence of systemic toxicity.

Ten Hla:(ICR)CVF male mice, approximately 4 weeks old and weighing 18-22 grams at injection were divided into two groups to receive either Solution 3 (test article) or 0.9% sodium chloride (control article). Mice have historically been used to evaluate potential toxicity of test articles. Each animal was injected via the intraperitoneal route with a dose of 25 mL/kg of either test article or control article. The test and control animals were observed for adverse reactions immediately after dosing and at 1 and 4 hours after injection and daily for 7 days. The animals were also weighed daily for 7 days after dosing. If during the observation period, none of the animals treated exhibited a significantly greater reaction than the control animals, the test article met the test requirements. If two or more animals died, or if abnormal behavior such as convulsions or prostration occurred in two or more animals, or if body weight loss greater than 2 grams occurred in three or more animals, the test article did not meet the test requirements.

Results of the tests are shown in Tables 5 and 6 below:

TABLE 5

Mortality and Body Weight Data:

| Animal Number | Weight (g) | | | | | | | #Dead/ #Tested |
|---|---|---|---|---|---|---|---|---|
| | Day 0 | Day 1 | Day 2 | Day 3 | Day 4 | Day 5 | Day 6 | Day 7 | |

Test Article

| 66 | 21 | 22 | 23 | 24 | 25 | 27 | 28 | 29 | 0/5 |
| 67 | 21 | 22 | 24 | 24 | 26 | 26 | 27 | 29 | |
| 68 | 21 | 22 | 24 | 25 | 26 | 27 | 28 | 29 | |
| 69 | 22 | 23 | 24 | 26 | 27 | 28 | 29 | 30 | |
| 70 | 18 | 19 | 20 | 20 | 22 | 23 | 23 | 24 | |

Control Article

| 61 | 20 | 21 | 22 | 23 | 24 | 25 | 26 | 26 | 0/5 |
| 62 | 21 | 22 | 23 | 24 | 25 | 27 | 28 | 29 | |
| 63 | 18 | 20 | 21 | 22 | 24 | 25 | 26 | 27 | |
| 64 | 20 | 20 | 22 | 23 | 24 | 26 | 26 | 27 | |
| 65 | 19 | 21 | 22 | 23 | 24 | 25 | 26 | 27 | |

TABLE 6

Clinical Observations:

| | Animal Number | | | |
|---|---|---|---|---|
| Time of Observation | 66 Test Article | 61 Control Article | 67, 68, 69, 70 Test Article | 62, 63, 64, 65 Control Article |
| Immediate | Normal | Normal | Normal | Normal |
| 1 hour | Normal | Normal | | |
| 4 hour | Normal | Normal | Normal | Normal |
| Day 1 | Normal | Normal | Normal | Normal |
| Day 2 | Normal | Normal | Normal | Normal |
| Day 3 | Normal | Normal | Normal | Normal |
| Day 4 | Normal | Normal | Normal | Normal |
| Day 5 | Normal | Normal | Normal | Normal |
| Day 6 | Normal | Normal | Normal | Normal |
| Day 7 | Normal | Normal | Normal | Normal |

As evidenced above, there was no mortality or evidence of systemic toxicity from the present invention injected into mice.

Dermal Contact Sensitization

The Dermal Contact Sensitization Test was performed in accordance with the requirements of International Organization for Standardization (ISO 10993-10): Biological Evaluation of Medical Devices—Part 10: Tests for Irritation and Delayed-Type Hypersensitivity. The study was conducted in accordance with the provisions of the FDA Good Laboratory Practice (GLP) Regulations (21 CFR, Part 58) evaluating Solution 3 (test article) for delayed dermal contact sensitization in a guinea pig maximization test. Following intradermal injection and occlusive patching of the test and control articles, Solution 3 showed no evidence of causing delayed dermal contact sensitization in the guinea pig. Dose determinations prior to testing established that the test article would be used at 100% concentration. Ten HlaHA)CVF Hartley albino guinea pigs were injected with the test article and five guinea pigs (same strain) were injected with the control article (0.9% Sodium Chloride). The Hartley albino guinea pig has been used historically for sensitization studies. The guinea pig is believed to be the most sensitive animal model for this type of study. The fur over the dorsoscapular region was removed and three rows of intradermal injections (two injections per row) were given to each animal within an approximate 2 cm×4 cm boundary of the fur clipped area as illustrated below.

Induction 1:
Control Animals:
a. 0.1 mL of 50/50 (v/v) mixture of Freund's Complete Adjuvant (FCA) and the control article
b. 0.1 mL of the control article
c. 0.1 mL of a 1:1 mixture of the 50/50 (v/v) control article/ FCA mixture and the control article
Test Animals:
a. 0.1 mL of a 50/50 (v/v) mixture of Freunds Complete Adjuvant (FCA) and the control article
b. 0.1 mL of the test article
c. 0.1 mL of a 1:1 mixture of the 50/50 (v/v) control article/ FCA mixture and the test article To minimize tissue sloughing the "a" and "c" injections were slightly deeper than the "b". The site "c" injection was administered slightly more caudal than site "b".

Induction 2:

At 6 days (±1 day) after completion of the 'Induction 1 injection', the fur over the dorsoscapular region (same area as used during Induction 1) of each animal was removed with an electric clipper. The area was treated with a 10% (w/v) Sodium Lauryl Sulfate (SLS) suspension in petroleum sufficient to coat the skin. The SLS suspension, applied to provoke a mild acute inflammation, was massaged into the skin over the injection site. The area was left uncovered. At 24 hours (±2 hours), any remaining SLS residue was gently removed with a gauze pad. An approximate 2 cm×4 cm section of filter paper, saturated with 0.3 mL of test article, was then topically applied to the previously injected sites of the test animals. The control animals were similarly patched with the control article. Each patch was secured with a non-reactive tape and the trunk of each animal was wrapped with an elastic bandage. At 48 hours, the bandages and patches were removed.

Challenge:

At 14 days (±1 day) after completion of Induction 2, the fur was removed from the sides and flank areas with an electric clipper. Non-woven cotton disks containing in a Hill Top Chamber were saturated with 0.3 mL of the test article or the control article. The test article was applied to the right flank of each animal and the control article was applied to the left flank of each animal. The trunk of each animal was wrapped with an elastic bandage to maintain well occluded sites. At 24 hours, the wraps and Hill Top Chambers were removed. Any residue remaining at the sites was removed. Observations for dermal reactions were conducted at 24 and 48 hours after challenge patch removal. Prior to each scoring procedure, the sites were wiped with 35% isopropyl alcohol. If necessary, the fur was removed from each site to facilitate scoring. Dermal reactions were scored in accordance with the criteria shown below in Table 7:

TABLE 7

| Patch Test Reaction | Grading Scale |
|---|---|
| No visible change | 0 |
| Discrete or patchy erythema | 1 |
| Moderate and confluent erythema | 2 |
| Intense erythema and swelling | 3 |

Animals were observed daily for general health and body weights were recorded at pretreatment. Individual results of dermal scoring for the challenge phase are provided in Table 8 below. Also provided are the results of the last periodic positive control study using 1-chloro-2,4-dinitrobenzene (DNCB) as positive control.

TABLE 8

TEST ARTICLE OF PRESENT INVENTION

| | | Dermal Reactions | | | |
|---|---|---|---|---|---|
| | | 24 Hour Score | | 48 Hour Score | |
| Treatment Group | Animal Number | Control Site | Test Site | Control Site | Test Site |
| Test | 2600 | Removed from study for humane reasons | | | |
| | 2601 | 0 | 0 | 0 | 0 |
| | 2602 | 0 | 0 | 0 | 0 |
| | 2603 | 0 | 0 | 0 | 0 |
| | 2604 | 0 | 0 | 0 | 0 |
| | 2935 | 0 | 0 | 0 | 0 |
| | 2937 | 0 | 0 | 0 | 0 |
| | 2944 | 0 | 0 | 0 | 0 |
| | 2954 | 0 | 0 | 0 | 0 |
| | 2959 | 0 | 0 | 0 | 0 |
| Negative Control | 2126 | 0 | 0 | 0 | 0 |
| | 2129 | 0 | 0 | 0 | 0 |
| | 2130 | 0 | 0 | 0 | 0 |
| | 2131 | 0 | 0 | 0 | 0 |
| | 2928 | 0 | 0 | 0 | 0 |
| LAST PERIODIC POSITIVE CONTROL - PERFORMED AUG. 14, 2010 | | | | | |
| Positive Control Using DNCB | 22 | 0 | 1 | 0 | 1 |
| | 23 | 0 | 1 | 0 | 1 |
| | 74 | 0 | 1 | 0 | 1 |
| | 257 | 0 | 2 | 0 | 2 |
| | 407 | 0 | 1 | 0 | 1 |
| | 410 | 0 | 1 | 0 | 1 |
| | 414 | 0 | 1 | 0 | 2 |
| | 417 | 0 | 1 | 0 | 2 |
| | 426 | 0 | 2 | 0 | 2 |
| | 428 | 0 | 2 | 0 | 2 |
| Negative Control | 19 | 0 | 0 | 0 | 0 |
| | 21 | 0 | 0 | 0 | 0 |
| | 122 | 0 | 0 | 0 | 0 |
| | 135 | 0 | 0 | 0 | 0 |
| | 187 | 0 | 0 | 0 | 0 |

Conclusion: The known sensitizer, DCNB produced evidence of causing delayed dermal contact sensitization in the Hartley strain of guinea pig confirming the methodology as valid. The present invention showed no evidence of causing delayed dermal contact sensitization in the guinea pig. ISO 10993-10 indicates that a minimum of 10 test animals shall be treated with each test sample and a minimum of five animals shall act as a solvent control group. On day 2 of the study, animal 2600 was removed from the study for humane reasons. This resulted in nine test animals remaining in the test group. All nine test animals had scores of "0" at both 24 hours and 48 hours, which was identical to the scores of the control animals. Due to the consistency of the data for the test animals, results from nine animals were considered sufficient to draw valid conclusions and thus did not have any impact on testing.

Oral Toxicity

The Oral Toxicity Test was performed in accordance with the guidelines of the Federal Hazardous Substances Act (FHSA) Regulations, 16 CFR 1500. There was no mortality or significant evidence of toxicity observed in the test animals (rats). Solution 3 (test article) would not be considered toxic at a dose of 5 g/kg by the oral route in the rat. Ten Hla:(SD) CVF, five male and five female rats, weighing 215-243 grams at dosing were dosed by gavage (the oral route) with the preferred embodiment of the present invention (test article). The rat has historically been used to establish hazardous substance labeling data. The oral route of dosing is selected as the strongest challenge for materials that could be accidentally ingested. The food for each rat was removed from each cage 16-20 hours prior to dosing. Each rat was weighed and gavaged with the test article via a stainless steel blunt-tipped cannula at a dose of 5 g/kg of body weight. The animals were then returned to their cages and food was returned after treatment. Animals were observed immediately after dosing, at 4 hours, and daily for up to 14 days for signs of illness or mortality. Body weights were recorded at dosing and at 14 days. At termination of the study, animals were euthanized and their viscera inspected by macroscopic examination. Based on the FHSA Regulations, a substance is considered "toxic" if it produces death within 14 days in 50% or more of a group of rats dosed with a single 50 mg/kg to 5 g/kg dose. All animals were clinically normal throughout the 14 day study, no animals died during the 14 day study, body weight data were acceptable, and there were no macroscopic changes in the viscera at necropsy that could be attributed to the single oral dose. Individual observations appear in Table 9 below:

TABLE 9

| Animal | | Body Weight (g) | | Clinical Observations | Necropsy |
|---|---|---|---|---|---|
| Number | Sex | Day 0 | Day 14 | (Days 0-14) | Day 14) |
| 7664 | Male | 240 | 337 | | |
| 7665 | Male | 243 | 356 | Normal | Macroscopically Normal |
| 7666 | Male | 236 | 324 | Normal | Macroscopically Normal |
| 7667 | Male | 243 | 339 | Normal | Macroscopically Normal |
| 7668 | Male | 243 | 355 | Normal | Macroscopically Normal |
| 7671 | Female | 215 | 242 | Normal | Macroscopically Normal |
| 7672 | Female | 226 | 255 | Normal | Macroscopically Normal |
| 7673 | Female | 222 | 249 | Normal | Macroscopically Normal |
| 7674 | Female | 228 | 262 | Normal | Macroscopically Normal |
| 7675 | Female | 220 | 247 | Normal | Macroscopically Normal |
| | Mean: | 232 | 297 | Normal | Macroscopically Normal |

All of the above safety studies (cytotoxicity, intracutaneous reactivity, systemic toxicity, dermal contact sensitization and oral toxicity) were conducted with Solution 3 (isotonic formulation of $K^+$, $Rb^+$, $Ca^{2+}$, $Zn^{2+}$ $Mg^{2+}$, $Br^-$ ±potassium sorbate as preservative) as the test article. Since this solution contained the ions present in Solution 2 and Solution 4, one of ordinary skill in the art could conclude that the safety study results similarly apply to these solutions as well.

Ciliotoxicity

Mouse septal explants were harvested and placed in a glass perfusion chamber on a thermostatically controlled stage. The chamber was filed with Locke Ringer's solution (136 mM NaCl, 5.6 mM KCl, 10 mM HEPES, 14.3 mM NaHCO3, 1.2 mM MgCl2, 2.2 mM CaCl2 and 11.5 mM dextrose, pH 7.35) and the temperature maintained between 35.5° C. and 37° C. Images were visualized microscopically using a water immersion 63× objective and differential interference contrast optics. Images were captured using a high-speed monochromatic digital video camera at a sampling rate of 100 frames per second and analyzed using virtual instrumentation software highly customized to perform cilia beating frequency (CBF) analysis. Recordings were made every 30 seconds for 10 minutes. Once a stable baseline of CBF was obtained (5-10 min) the Locke Ringer's solution was replaced by solutions containing various compositions of metal ions while maintaining visualization of the beating cilia. Recordings continued for 10 min. In such fashion ciliotoxicity was determined. The formulations of the present invention that were tested in sterile solutions included:

A. Isotonic formulation of $K^+$, $Rb^+$, $Ca^{2+}$, $Zn^{2+}$±potassium sorbate as preservative (Solution 2)
B. Isotonic formulation of $K^+$, $Rb^+$, $Ca^{2+}$, $Zn^{2+}$ $Mg^{2+}$, $Br^-$±potassium sorbate as preservative (Solution 3)
C. Hypertonic formulation of $K^+$, $Rb^+$, $Ca^{2+}$, $Zn^{2+}$ $Mg^{2+}$, $Br^-$±potassium sorbate as preservative (Solution 1+$Mg^{2+}$, $Br^-$)

Figure 1B:
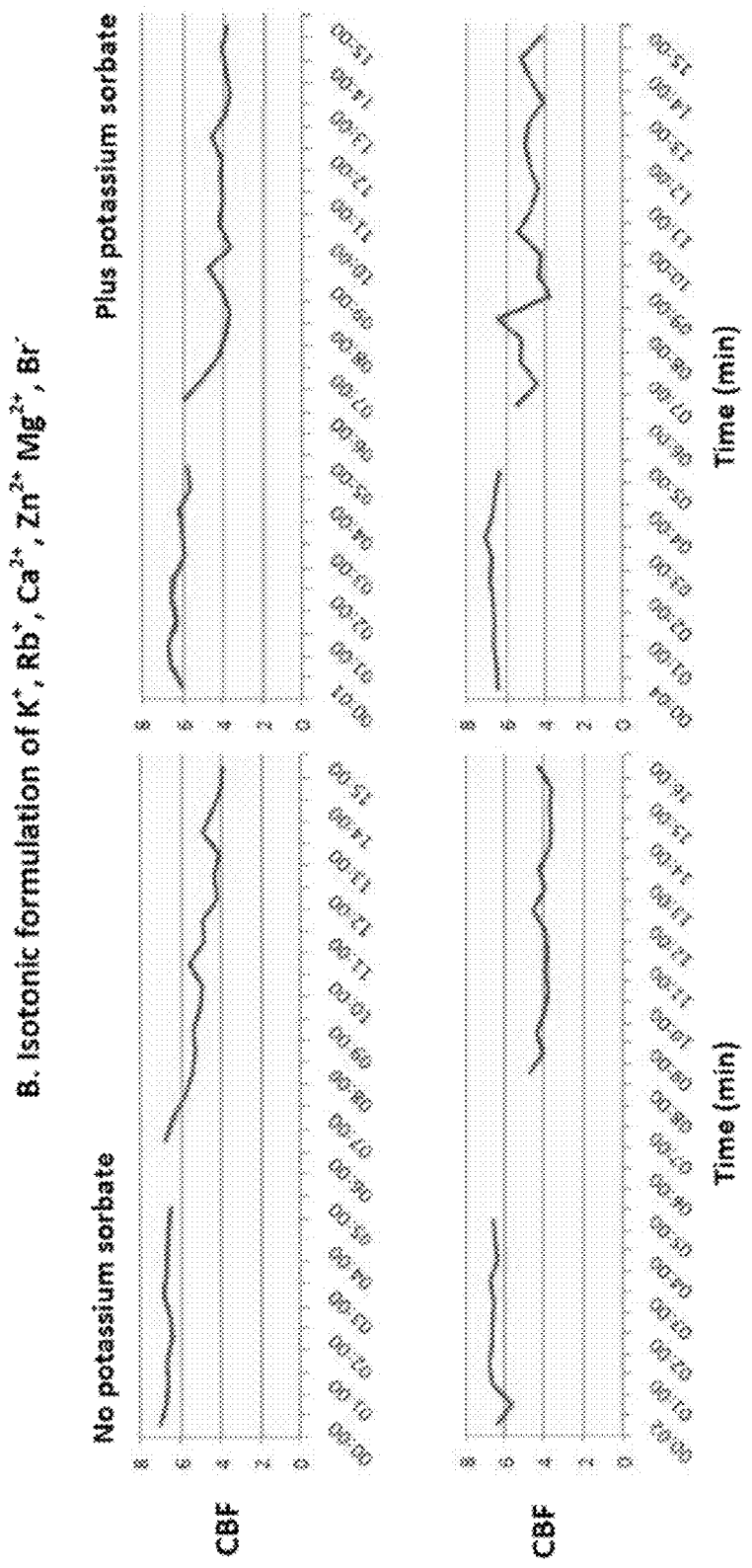
Figure 1C:
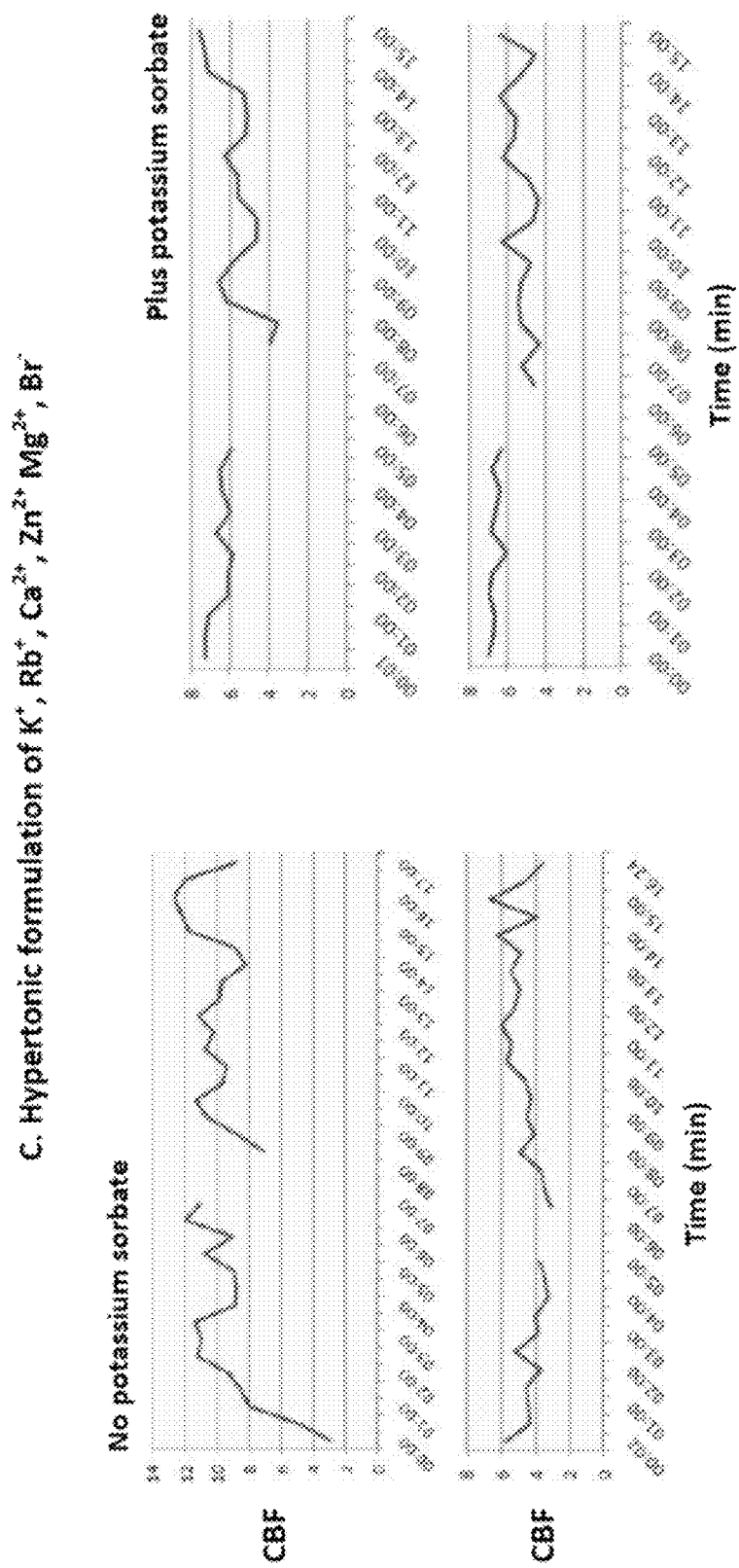

The tracings in FIG. 1 indicate that none of the formulations of the present invention produced any acute ciliotoxicity in the mouse explants model. On the left hand side of each tracing is the cilial beating frequency in Locke Ringer's solution and after the break in each trace, the cilial beating frequency of the cells immersed in the indicated formulation of the present invention are represented.

EXAMPLE 1

Efficacy for the Treatment of Sinonasal Injury

To evaluate efficacy, a live rabbit model of maxillary sinus injury was used to test the ability of the present invention to cause re-epithelialization of the rabbit maxillary sinus mucosa after surgical trauma.

*Pasteurella*-free New Zealand white rabbits underwent maxillary sinus surgery. In the first experiment, surgery was performed to completely remove the left maxillary sinus mucosa while only the mucosa of the medial wall was removed on the right side. After mucosal stripping, the periosteal flaps were repositioned and the skin incision was closed with sutures. Rabbits were sacrificed at 2, 7, 15, and 22 days post surgery and the snouts sectioned and processed for hematoxylin and eosin staining for analysis of mucosal regeneration. A qualitative grading of the epithelia was performed. Twelve symmetrically distributed points of each maxillary sinus were evaluated by light microscopy. The epithelium found was classified as normal respiratory, transitional or squamous epithelium.

Figure 2:
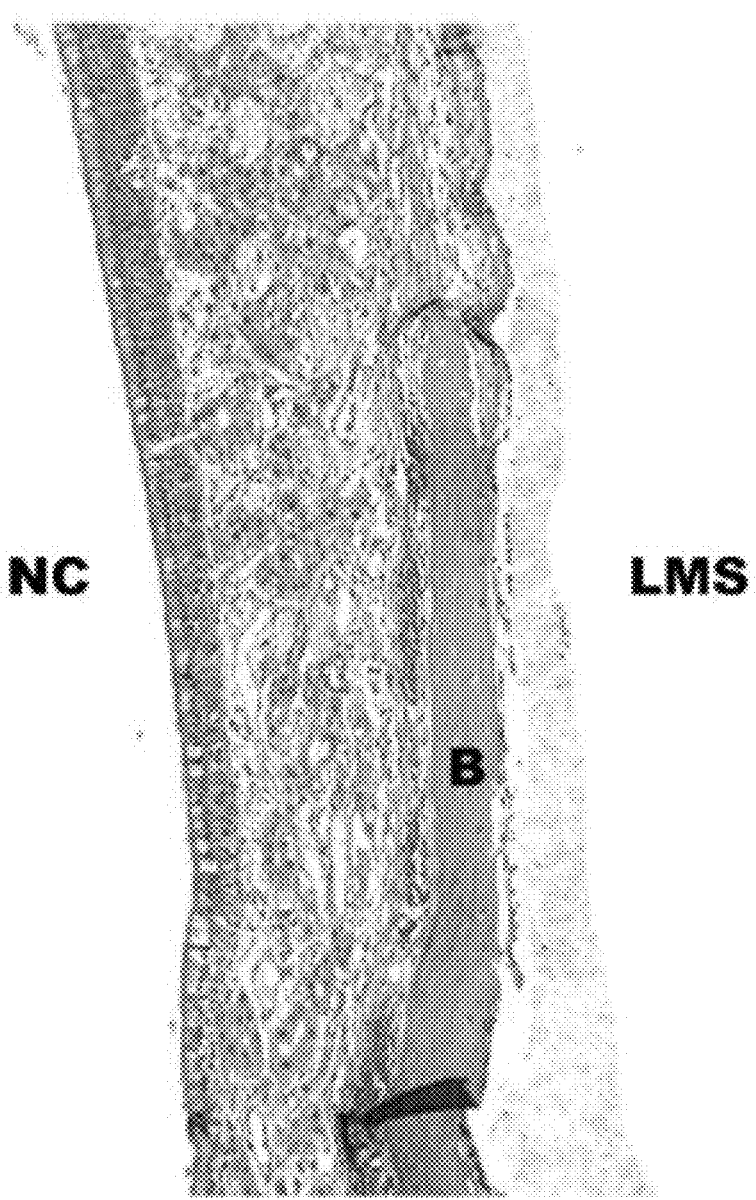
FIG. 2 is an image depicting the nasal cavity (NC) epithelium as contrasted against the Left Maxillary Sinus (LMS) after a sinus mucosal stripping procedure in which no treatment is administered. Two days post-operatively no epithelia are observed and a fibrous material covers the sinus walls. Denuded bone (B) is present.

Results:

No Treatment:

Two days after the sinus mucosal stripping procedure a medial ulceration was seen in the right maxillary sinus, while an almost complete absence of epithelium was evidenced on the left sinus. The walls were covered by a fibrinous matrix with numerous red blood cells, platelets and inflammatory cells. Areas of denuded bone were also seen (FIG. 2).

Figure 5:
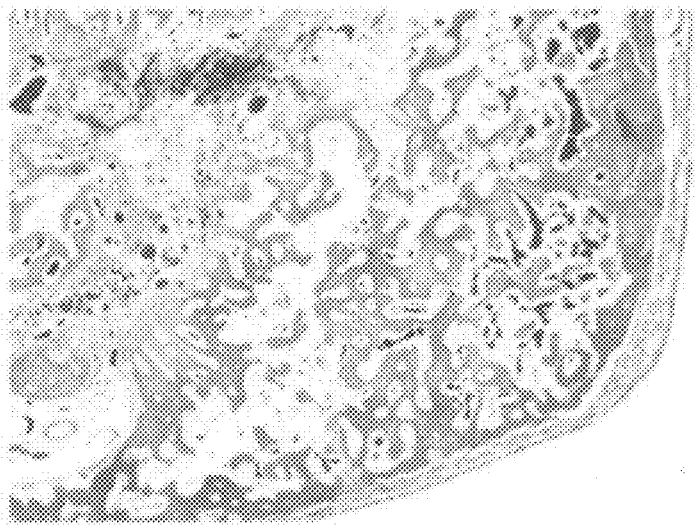
FIG. 5 is an image of the LMS 22 days after mucosal removal illustrating complete obliteration of the anterior portion of the LMS.
Figure 4:
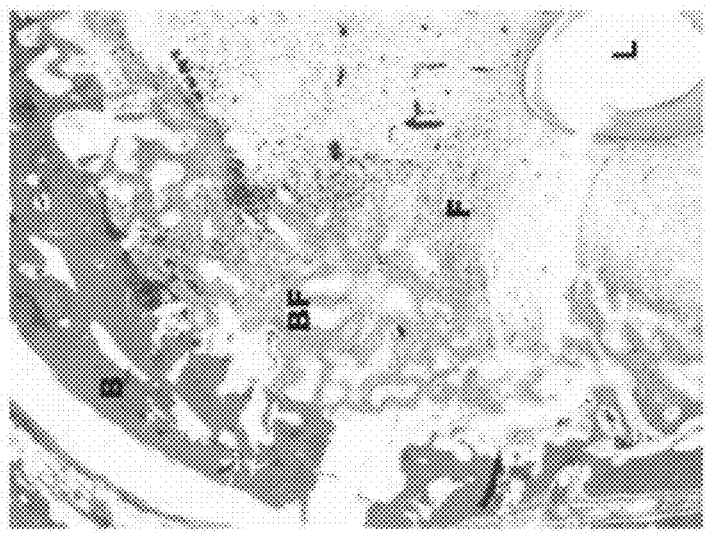
FIG. 4 is an image of the LMS fifteen days after mucosal removal. As depicted in the image, the LMS has been almost obliterated by fibrosis and concentric neo-ontogenesis, with only a small remnant of a lumen. Note the mature bone (B), concentric bone formation (CBF), fibrosis (F) and remnant of lumen (L).
Figure 3:
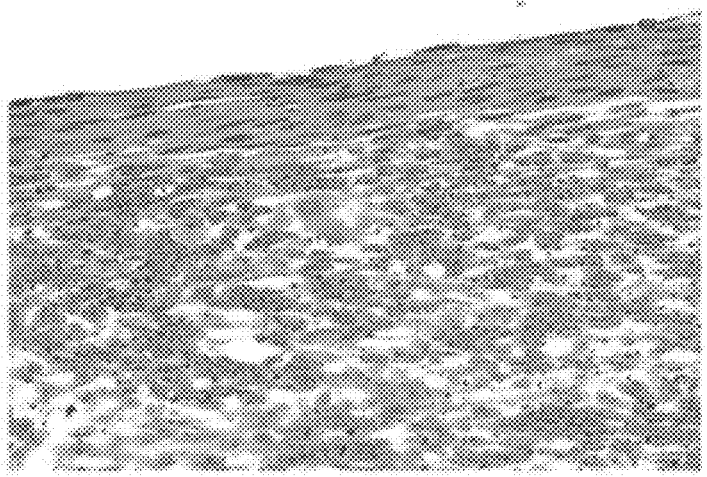
FIG. 3 is an image depicting the nasal cavity seven days post-operatively with no treatment administered. A "transitional" squamous epithelium is observed over an inflammatory collagenous matrix.

Seven days after the mucosal stripping procedure, ulcerated areas were evident, covered by transitional squamous epithelium, however, patchy areas of ulceration still existed (FIG. 3). By the end of the second week bone formation was observed on the left side. The anterior portion of the left maxillary sinus had been nearly completely obliterated by fibrosis and concentric neo-osteogenesis, with tiny remnant of a lumen (FIG. 4), while at three weeks complete obliteration is evident (FIG. 5, low power).

The remaining portions of the sinuses were fully covered by epithelium. Forty-one point six (41.6%) (20/48) of the remaining posterior left sinus was composed of squamous epithelium, with small areas of differentiation (cuboidal or cylindrical ciliated epithelia). On the right sinus, 39.5% (19/48) of the posterior sections were covered by a squamous epithelium; but the anterior sections were almost completely covered by a squamous epithelium (77%).

Figure 6:
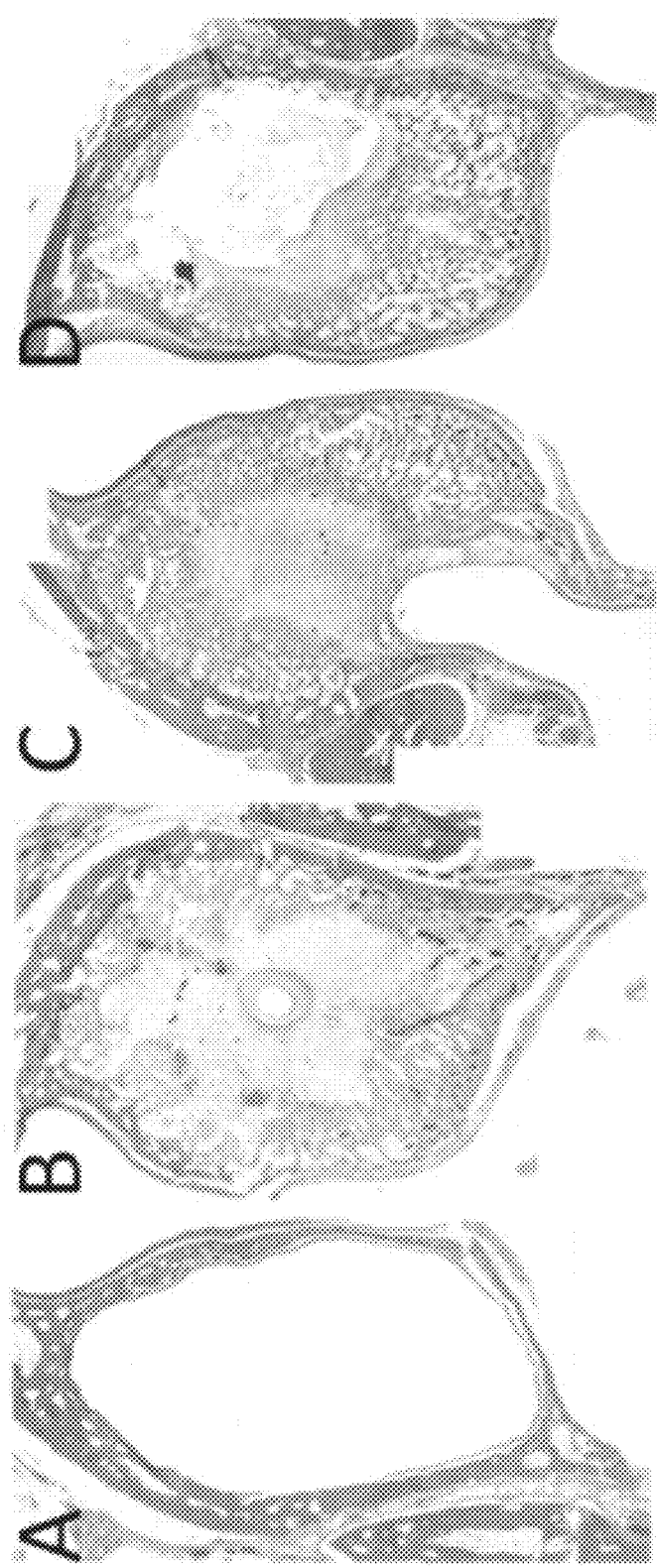
FIG. 6 is a series of images depicting the nasal cavity two weeks after mucosal stripping and treatment with either saline or an isotonic solution containing $K^+$, $Rb^+$, $Ca^{2+}$, and $Zn^{2+}$ (Solution 2) without the preservative potassium sorbate. (A) medial wall injury with no intervention; (B) complete mucosal stripping with no intervention; (C) complete mucosal stripping with daily saline irrigation (3 cc); (D) complete mucosal stripping with daily irrigation (3 cc) with a metal ion Solution 2 (sterile isotonic formulation of $K^+$, $Rb^+$, $Ca^{2+}$, $Zn^{2+}$ without the preservative potassium sorbate).

The effects of the present invention on sinonasal mucosal healing were then investigated in this animal model. A slight modification of the protocol used for the above studies included the insertion of an irrigating catheter into the nasal passages of the rabbits. Complete mucosa stripping was performed with once daily irrigation of 3 cc (equivalent to 3 mL or about 0.1 oz.) of either saline solution or metal ion solution for two weeks (FIG. 6).

Treatment with the Present Invention:

Pixel analysis of the complete mucosal stripping of sinuses (FIGS. 6B, C and D) demonstrates that daily irrigation of the nasal passages with the present invention significantly inhibited osteoneogenesis compared to either no treatment or treatment with normal saline (TABLE 10).

TABLE 10

| Rabbit | pixels | | |
| --- | --- | --- | --- |
| | Lumen | Sinus Area | % |
| No Treatment | 94,366 | 4739642 | 1.99 |
| Daily irrigation with Normal Saline | 336,846 | 4103053 | 8.21 |
| Daily irrigation with metal ion solution | 1,083,097 | 3974206 | 27.25 |

Compared to daily saline irrigation, which demonstrated some inhibition of osteoneogenesis compared to no treatment (8.21% vs 1.99%), daily irrigation with present invention Solution 2 (sterile isotonic formulation of K+, Rb+, Ca2+, Zn2+ without preservative) resulted in significant increase of the lumen (27.25%).

EXAMPLE 2

Enhancement of Post-Surgical Sinonasal Recilialization

In addition to decreasing osteoneogenesis, daily irrigation with metal ion solutions also increase the rate of recilialization of the medial wall in sinonasal passages in the rabbit compared to daily saline irrigation.

In a follow-up experiment, nine New Zealand White rabbits underwent bilateral medial wall maxillary mucosal stripping followed by placement of maxillary sinus indwelling irrigating catheters. In this way, each nostril in each rabbit could be irrigated with different solutions for 14 days.

Both the sides of the nose, and the therapy were randomized in the rabbits as follows: one side of the nose in each rabbit was irrigated once daily (3 cc) with normal saline solution to act as a control for the other side. In five of the rabbits the other side of the nose was irrigated once daily (3 cc) with metal ion Solution 2 (sterile isotonic formulation of $K^+$, $Rb^+$, $Ca^{2+}$, $Zn^{2+}$ without preservative) and in the other four rabbits, the other side of the nose was irrigated daily (3 cc) with metal ion solution 3 (sterile isotonic formulation of $K^+$, $Rb^+$, $Ca^{2+}$, $Zn^{2+}$, $Mg^{2+}$, $Br^-$ without preservative).

At the completion of the therapeutic trial, snouts were harvested and remucosalization with ciliated cells was assessed at the site of injury by hematoxylin and eosin (H&E) staining as well as immunohistochemistry for type IV tubulin, a marker of motile cilia. Semi quantitative grading of reciliation was done by two blinded observers [0=no cilia; 1=<30% cilia; 2=30-60% cilia; 3=>60% cilia]. Statistical significance in ciliation was determined using a one-tailed unpaired Student's t-test.

Figure 7:
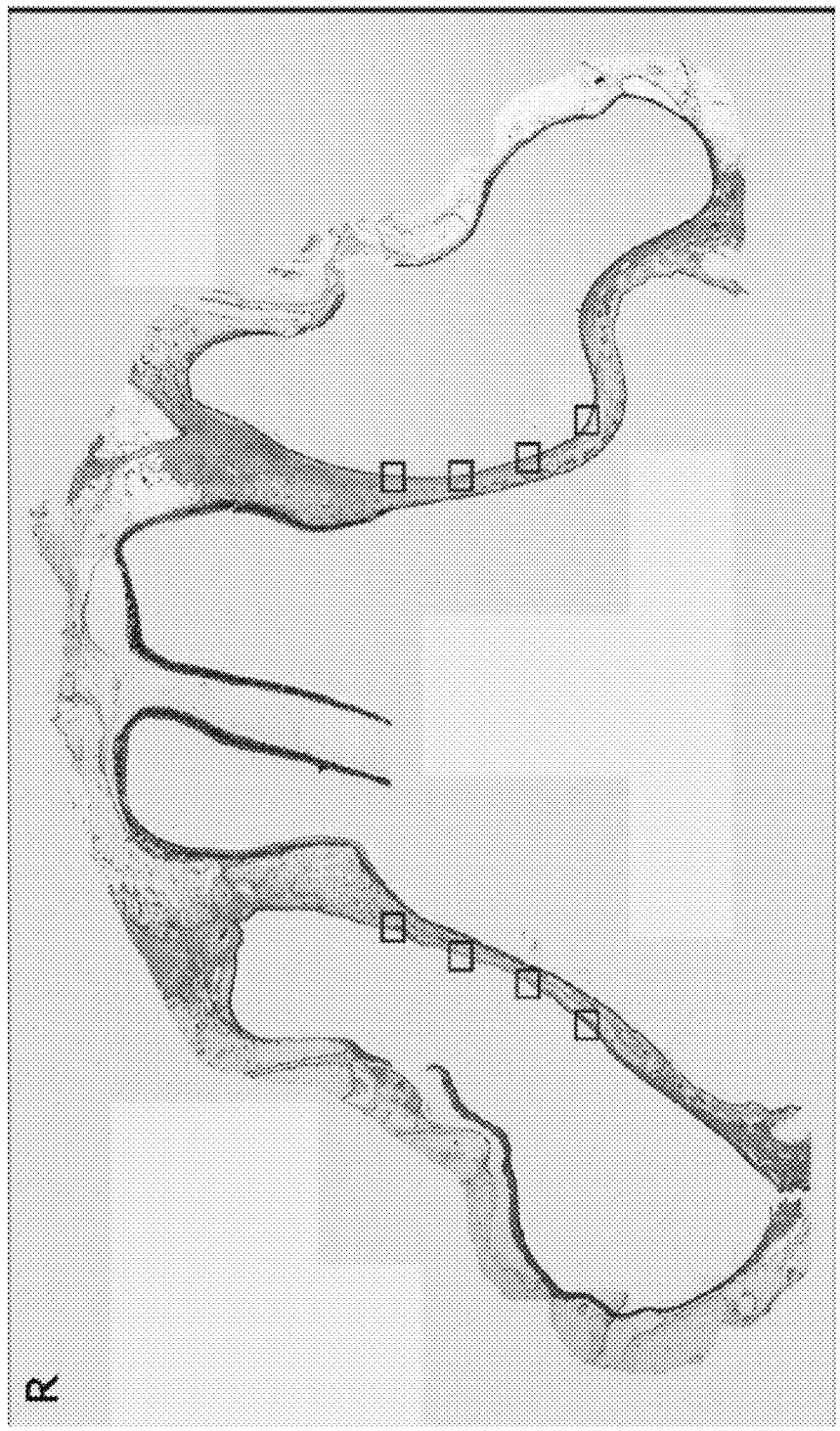
FIG. 7 is an image of a representative rabbit snout with positions on the "injured" medial wall indicated (boxes) where four images were taken for analysis of ciliated remucociliazation. Images were also taken from the uninjured lateral wall to represent normal ciliation of the mucosal wall.
Figures 10A, 10B:
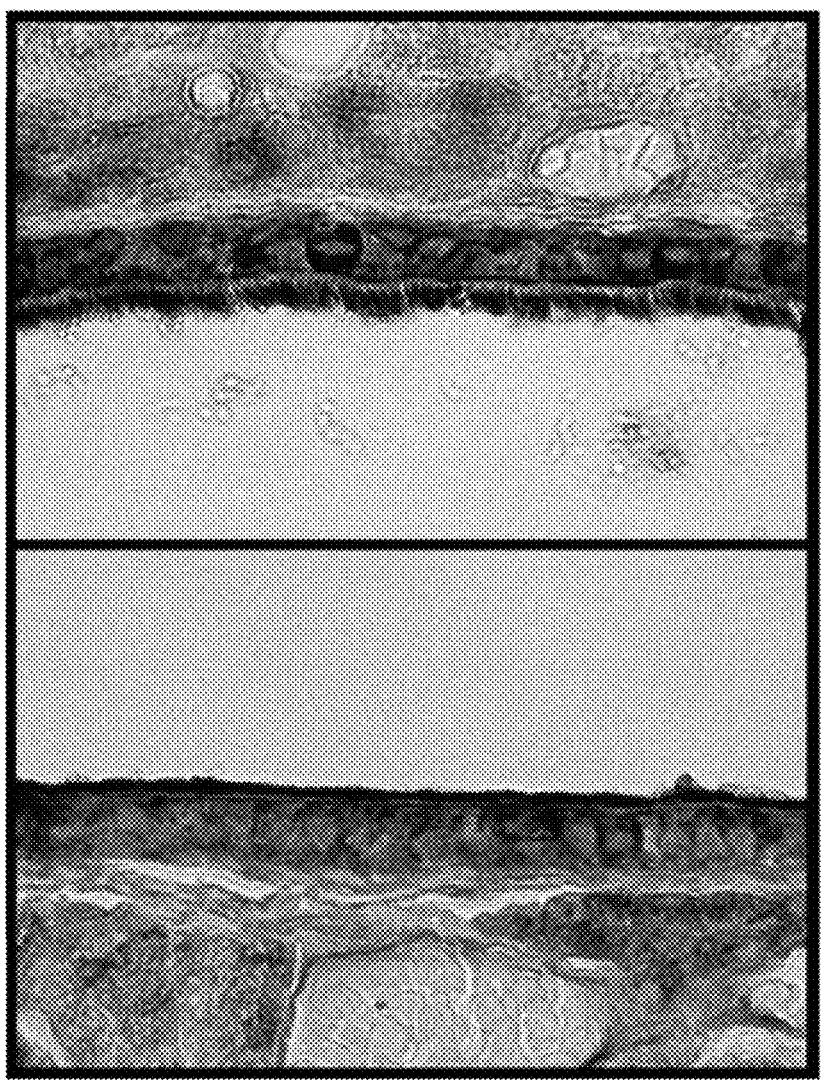
FIG. 10 is a series of images from the injured lower medial wall that are Type IV β-tubulin-stained. (A) a maxillary sinus treated with saline and (B) a maxillary sinus treated with a sterile isotonic formulation of $K^+$, $Rb^+$, $Ca^{2+}$, $Zn^{2+}$ (Solution 2) without the preservative potassium sorbate. As shown in (B), daily treatment with the isotonic formulation of $K^+$, $Rb^+$, $Ca^{2+}$, $Zn^{2+}$ (Solution 2) without the preservative potassium sorbate has resulted in recilialization.

FIG. 7 shows a representative rabbit snout outlined by immunohistochemistry using type IV-tubulin staining. The positions on the medial walls of each snout where four evenly distributed images were obtained for both H&E and type IV-tubulin (cilia) staining are indicated. FIG. 8 is an image taken from the uninjured lateral wall and depicts normal mucosal ciliation. FIGS. 9 and 10 are images that are stained with type-IV b-tubulin from the upper and lower medial wall 14 days after surgery and treatment with either saline (FIGS. 9A and 10A) or an isotonic formulation of $K^+$, $Rb^+$, $Ca^{2+}$, and $Zn^{2+}$ without the preservative potassium sorbate (Solution 2) (FIGS. 9B and 10B).

The results of remucosalization with ciliated cells was assessed at the site of injury by two blinded observers of hematoxylin and eosin (H&E) stained sections as well as immunohistochemistry for type IV tubulin, a marker of motile cilia. The sections were graded 0, 1, 2, or 3 according to the density of cilia in the sections and the results are summarized in TABLE 11.

TABLE 11

| Type of Staining | Treatment | | |
|---|---|---|---|
| | Saline (n = 9) | Solution 2[a] (n = 5) | Solution 3[b] (n = 4) |
| H & E[c] | 1.33 | 2.43 | 2.72 |
| Type IV β-Tubulin | 1.68 | 2.33 | 2.88 |

[a]Sterile isotonic formulation of $K^+$, $Rb^+$, $Ca^{2+}$, $Zn^{2+}$ without preservative
[b]Sterile isotonic formulation of $K^+$, $Rb^+$ $Ca^{2+}$, $Zn^{2+}$, $Mg^{2+}$, $Br^-$ without preservative
[c]Hematoxylin and eosin

EXAMPLE 3

Figures 11C, 11D:
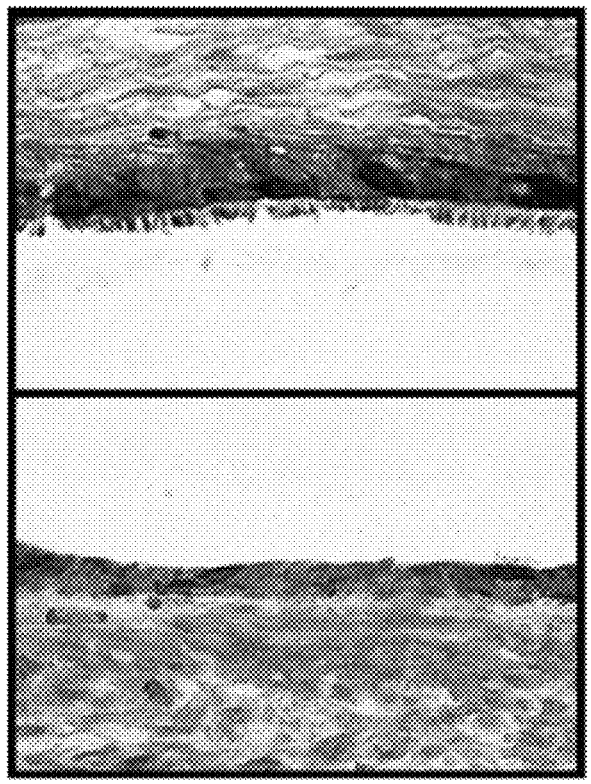
FIG. 11 is a series of images from the injured medial wall of the rabbit maxillary sinus in which sections of the medial maxillary sinus wall were surgically stripped of mucosal cells and treated for 14 days with either saline or an isotonic formulation of $K^+$, $Rb^+$, $Ca^{2+}$, $Zn^{2+}$, $Mg^{2+}$ and $Br^-$ (Solution 3) without the preservative potassium sorbate. (A) H&E staining of rabbit maxillary sinus treated with saline; (B) H&E staining of rabbit maxillary sinus treated with isotonic formulation of $K^+$, $Rb^+$, $Ca^{2+}$, $Zn^{2+}$, $Mg^{2+}$ and $Br^-$ (Solution 3) without the preservative potassium sorbate; (C) Type IV β-tubulin-staining of rabbit maxillary sinus treated with saline; (D) Type IV β-tubulin-staining of rabbit maxillary sinus treated with isotonic formulation of $K^+$, $Rb^+$, $Ca^{2+}$, $Zn^{2+}$, $Mg^{2+}$ and $Br^-$ (Solution 3) without the preservative potassium sorbate.
Figures 11A, 11B:
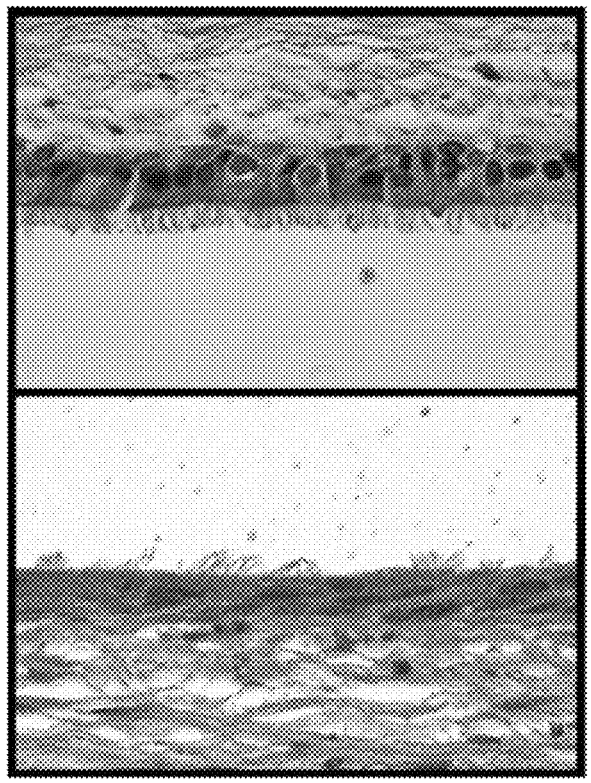

Based upon the results of Example 2, another study using 24 rabbits was performed in which Solution 3 was compared to Normal Saline, the normal standard of care for nasal irrigation treatment after Functional Endoscopic Sinus Surgery (FESS) in patients with chronic rhinosinusitis. Twenty four New Zealand White rabbits underwent bilateral medial wall maxillary mucosal stripping followed by placement of an indwelling irrigation catheter as described above. In a randomized fashion, one nasal passage received 3 cc of normal saline daily, while the contralateral nasal passage received 3 cc of Solution 3 daily. After a 14 day therapeutic trial, snouts were harvested and remucosalization was assessed by hematoxylin and eosin staining and immunohistochemical staining using type IV-tubulin, a marker of motile cilia. Reciliation grading was as described above using two blinded observers. FIG. 11 shows both H&E and immunohistochemical staining of sections of the medial maxillary sinus wall that had been surgically stripped of mucosal cells and treated for 14 days with either normal standard of care (saline), or solution 3. As can be seen, treatment using Solution 3 results in a significantly accelerated and enhanced healing of the medial wall. The frequency distribution of scores for remucosalization of the denuded medial maxillary sinuses with ciliated cells is given in TABLE 12.

TABLE 12

| Type of Staining | Type of Treatment | Cilial Density Score | | | |
|---|---|---|---|---|---|
| | | 0% | <30% | 30-60% | >60% |
| Hematoxylin & Eosin | Saline | 53 | 46 | 31 | 62 |
| | Solution 3 | 3 | 2 | 12 | 175 |
| Type IV β-Tubulin | Saline | 53 | 46 | 18 | 75 |
| | Solution 3 | 3 | 1 | 2 | 186 |

Hematoxylin and Eosin staining demonstrated that normal saline (n=24), the present standard of care for post-surgical treatment of chronic rhinosinusitis, had substantial bare areas with predominant ciliation scores under 30%. The group treated with Solution 3 (n=24) achieved a statistically significant improvement (using a Chi-square test to compare the frequency distributions in each group) in ciliary density (>60%) when compared with normal saline (p<0.01). These results were confirmed with Type IV β-Tubulin staining Success of Functional Endoscopic Sinus Surgery (FESS) depends on restoration of normal mucociliary clearance. Daily topical irrigation with Solution 3 (sterile isotonic formulation of $K^+$, $Rb^+$, $Ca^{2+}$, $Zn^{2+}$, $Mg^{2+}$, $Br^-$) significantly enhances ciliated remucosalization compared to saline.

EXAMPLE 5

An animal model to characterize the re-epithelialization of the rabbit maxillary sinus mucosa after surgical trauma was developed and the safety and efficacy of the wound repair accelerative topical preparation, with Solutions 2 or 3, was tested (Entent Care, Maitland, Fla.).

Materials and Methods
Solutions

A description of the original solution (Solution 1) can be found in U.S. Pat. No. 6,149,947, herein incorporated in its entirety by reference. Solution 1 is a specific hypertonic sinonasal formulation from a proprietary blend of mineral salts including potassium, calcium, zinc, and rubidium.

The inventors have developed several new solutions to enhance wound healing, particularly in the sinonasal mucosa. Solution 2 is a sterile isotonic formulation containing $K^+$, $Rb^+$, $Ca^{2+}$, and $Zn^{2+}$ without a preservative. Solution 3 is a sterile isotonic formulation containing $K^+$, $Rb^+$, $Ca^{2+}$, $Zn^{2+}$, $Mg^{2+}$, $SO_4^{2-}$, and $Br^-$ without a preservative.

Evaluation of Respiratory Ciliotoxicity

Mouse nasal septal explants were harvested as previously described. (Antunes M B, Woodworth B A, Bhargave G, et al. Murine nasal septa for respiratory epithelial air-liquid interface cultures. Biotechniques. 2007; 43:195-204). Once harvested, the septal mucosal explants were placed in a glass perfusion chamber on a thermostatically controlled stage, held in place with a nylon grid (1.5 mm) whose outer frame was snapped into the inside of the perfusion chamber as previously described. (Schipor I, Palmer J N, Cohen A S, et al. Quantification of ciliary beat frequency in sinonasal epithelial cells using differential interference contrast microscopy and high-speed digital video imaging. Am J Rhinol 2006; 20:124-127).

The chamber was filled with Locke Ringer's solution (136 mM NaCl, 5.6 mM KCl, 10 mM HEPES, 14.3 mM NaHCO3, 1.2 mM MgCl2, 2.2 mM CaCl2, and 11.5 mM dextrose, pH 7.35) and the temperature maintained between 35.5° C. and 37° C. with a dual channel heater (Warner Inst, Hamden, Conn.). Images were visualized using a Leica DMLFSA microscope set on an air table (TMC, Peabody, Mass.) using a water immersion 363 objective and differential interference contrast (DIC) optics (Leica Microsystems, Bannockburn, Ill.).

Images were captured using a model A602f-2 Basler high speed monochromatic digital video camera (Basler A G, Ahrensburg, Germany) at a sampling rate of 100 frames per second with a resolution of 640 3 480 pixels. The video images were analyzed using the Sisson-Ammons Video Analysis (SAVA) system version 2.1.18. For each experiment, beating cilia on the edge of the explant were detected with an upright microscope. The digital image signal was then routed from the camera directly into a digital image acquisition board (National Instruments) within a Dell XPS 710 Workstation running Windows XP Professional operating system. Images were captured, compressed, and stored to disk. Files were then reloaded and analyzed with virtual instrumentation software highly customized to perform CBF analysis. Recordings were made every 30 seconds for a total of 20 minutes.

Beating cilia were observed and recorded every 30 seconds for CBF determination. Once a stable baseline had been obtained (5 minutes), the test solution, either Solution 2 or Solution 3 (with or without 0.075% potassium sorbate as a preservative), was substituted for the Locke Ringer's solution while maintaining visualization of the beating cilia. Recordings continued for 10 minutes followed by replacement of the test solution with Locke Ringer's for an additional 5 minutes. Each solution was tested in duplicate.

In Vivo Efficacy of Solution 2 to Accelerate Mucosal Healing

Prior to any animal experimentation, approval was obtained from the Institutional Animal Care and Use Committee at the Philadelphia Veterans Affairs Medical Center (PVAMC). Nine New Zealand white rabbits were used. Exposure of the maxillary sinus mucosa bilaterally was performed as previously described. (Chiu A G, Antunes M B, Palmer J N, et al. Evaluation of the in vivo efficacy of topical tobramycin against *Pseudomonas* sinonasal biofilms. J Antimicrob Chemother. 2007; 59:1130-1134; Bleier B S, Palmer J N, Gratton M A, et al. In vivo laser tissue welding in the rabbit maxillary sinus. Am J Rhinol 2008; 22: 625-628; Bleier B S, Palmer J N, Sparano A M, et al. Laser-assisted cerebrospinal fluid leak repair: an animal model to test feasibility. Otolaryngol Head Neck Surg. 2007; 137:810-814).

Briefly, following a midline nasal dorsum skin incision, medially based periosteal flaps were elevated bilaterally. The anterior face of the maxillary sinus was removed with an otologic drill (XPS-3000, Medtronic Xomed Inc, Jacksonville, Fla.). Under microscopic visualization, a 131-cm mucosal flap was elevated, using otologic instruments, off the medial wall of the maxillary sinus and removed. Bilateral maxillary sinus indwelling irrigating catheters were then placed and secured as previously described. (Chiu A G, Antunes M B, Palmer J N, et al. Evaluation of the in vivo efficacy of topical tobramycin against *Pseudomonas* sinonasal biofilms. J Antimicrob Chemother. 2007; 59:1130-1134; Tamashiro E, Banks C A, Chen B, et al. In vivo effects of citric acid/zwitterionic surfactant cleansing solution on rabbit sinus mucosa. Am J Rhinol Allergy. 2009; 23:597-601).

Approximately 1.0 cm of tubing was placed into the sinus; the remainder was tunneled under the skin and brought out through a stab incision at the vertex of the cranium between the ears of the rabbit. Along the course of the catheter, vicryl sutures were used to drape the periosteum over the catheter. The hub of the tubing was capped and secured to the skin with a purse string suture of 3-0 nylon, and the midline incision was closed with a running 3-0 nylon. Patency of the catheter was checked by instilling 3 mL of normal saline (NS) or test solution and confirming drainage through the ipsilateral naris. Randomization of sinuses was performed prior to instillation of any solution. For each rabbit, one side received NS while the other side received either Solution 2 or Solution 3. Thus, each rabbit served as its own "saline" control, whereas the sides were randomized. Each sinus was irrigated daily with 3 mL of solution for 14 days. At the completion of the therapeutic trial, the rabbits were euthanized using sedation and an intracardiac barbiturate overdose.

Snouts were harvested, fixed for 24 hours in 10% normal buffered formalin, and then decalcified for 48 hours in rapid decalcifier (Electron Microscopy Sciences, Hatfield, Pa.). After sectioning, dehydrating, and paraffin embedding, the tissue was sectioned, and remucosalization with ciliated cells was assessed at the site of injury by hematoxylin and eosin (H&E) staining as well as immunohistochemistry (IHC) for type-IV β-tubulin, a marker of motile cilia.

The stripping was performed in the middle third of the medial wall of the maxillary sinuses, and 4 representative segments of regenerated mucosa were imaged at 340 magnification from each side. The micrographs from both H&E and IHC staining were assembled in random order and reviewed by 2 blinded trained observers. Thus, for each sinus evaluated, 8 data points for H&E and 8 data points for type IV β-tubulin immunohistochemistry were generated.

Figures 12A, 12B:
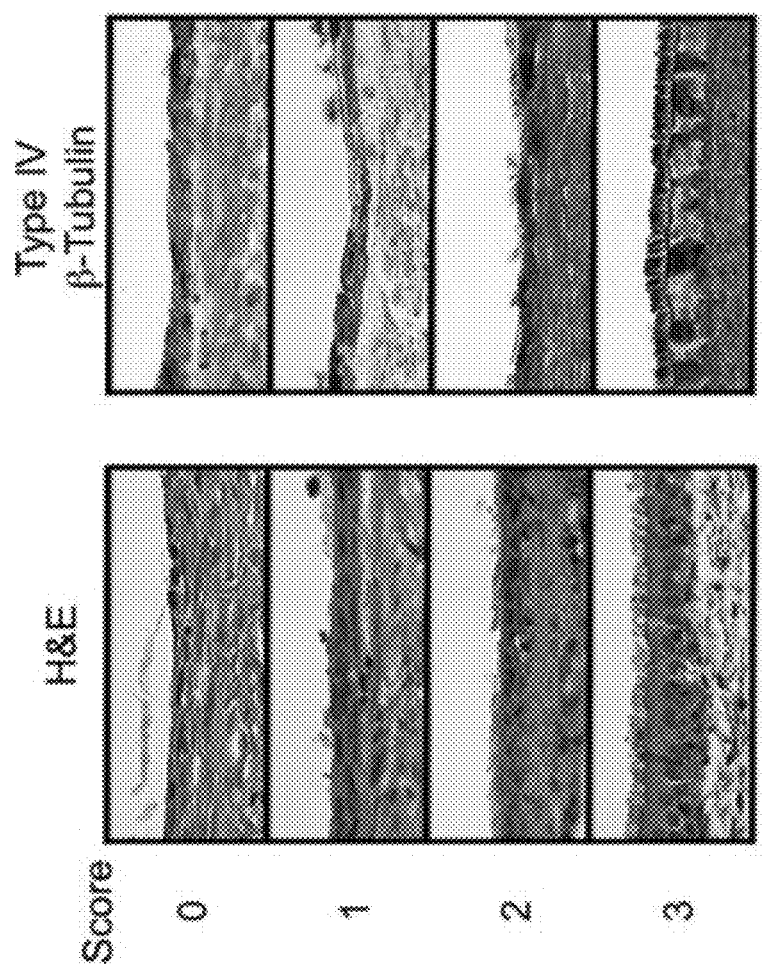
FIG. 12 is a series of images depicting a semi quantitative grading of reciliation. (A) sections of rabbit snout fixed and stained with hematoxylin and eosin; (B) sections of rabbit snout fixed and subjected to immunohistochemistry for type IV β-tubulin, a marker of respiratory cilia. 0=no cilia; 1=less than 30% cilia; 2=30% to 60% cilia; 3=greater than 60% cilia.

A semi quantitative grading of reciliation was used based on the amount of mucosa covered with cilia: 0=no cilia, 1=less than 30% cilia, 2=30% to 60% cilia, 3=greater than 60% cilia (FIG. 12). Given the categorical nature of the data sets of reciliation, the inventors applied the chi-square test to determine significance between each group using Prism 5 (GraphPad, La Jolla, Calif.). The animal protocol was IACUC approved.

Results

Ciliotoxicity Analysis

Figures 13A, 13B:
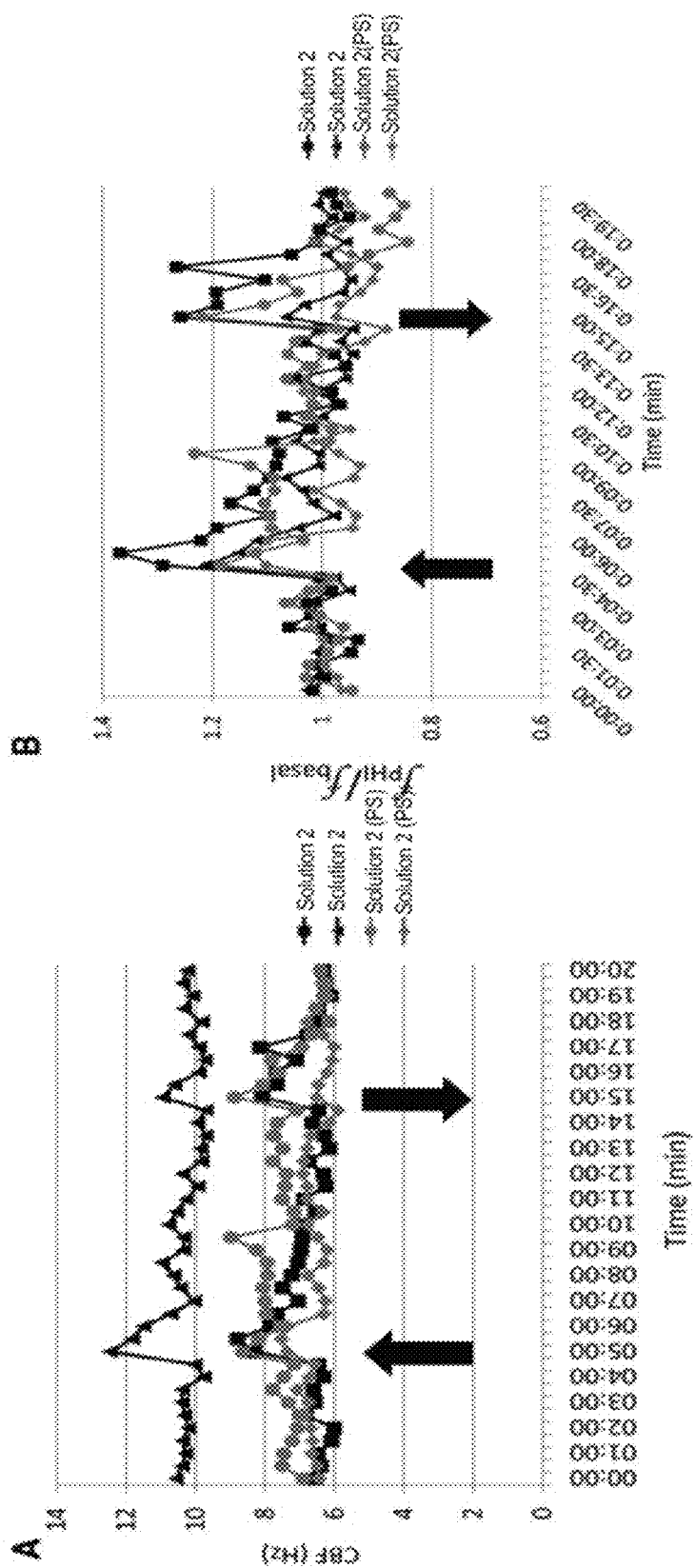
FIG. 13 is a series of images depicting that application of PHI with or without preservative does not affect murine septal ciliary beat frequency. (A) continuous recording and analysis of ciliary beat frequency from murine nasal septal explants demonstrates that application of Solution 2 (0.075% potassium sorbate) (up arrow) does not alter ciliary beat frequency. Additionally, replacement of Solution 2 with Locke Ringer's (down arrow) does not affect ciliary beat frequency. (B) normalization of ciliary beat frequency was performed to account for intrinsic differences in basal beat frequency of varying specimens. No alteration in $f_{PHI}/f_{basal}$ is evident (tracing between up and down arrow).

Ciliary beat frequency of murine septal mucosal explants was observed and quantified for 5 minutes in Locke Ringer's solution. The bathing solution was exchanged with Solution 2 (up arrow FIG. 13A, black tracings), and ciliary beat frequency was continuously monitored for an additional 10 minutes. Following these treatments, the bathing solution was once again exchanged to Locke Ringer's (down arrow FIG. 13, black tracings). The experiment was repeated with the addition of the preservative potassium sorbate (0.075%) (FIG. 13, gray tracings). Because each explant has a slightly different intrinsic basal ciliary beat frequency, the tracings were normalized by averaging the pretreatment baseline frequencies (T=0 to T=5 minutes) and dividing each individual frequency by the average basal frequency (fPHI/fbasal) (FIG. 13b).

As demonstrated in FIG. 13, the addition of Solution 2 had no effect on basal ciliary beat frequency. It should be noted that immediately after exchanging solutions (up and down arrow), there was an increase in ciliary beat frequency, which was most likely caused by mechanical perturbation of the epithelium and subsequent activation of mechanosensors.

Figures 14A, 14B:
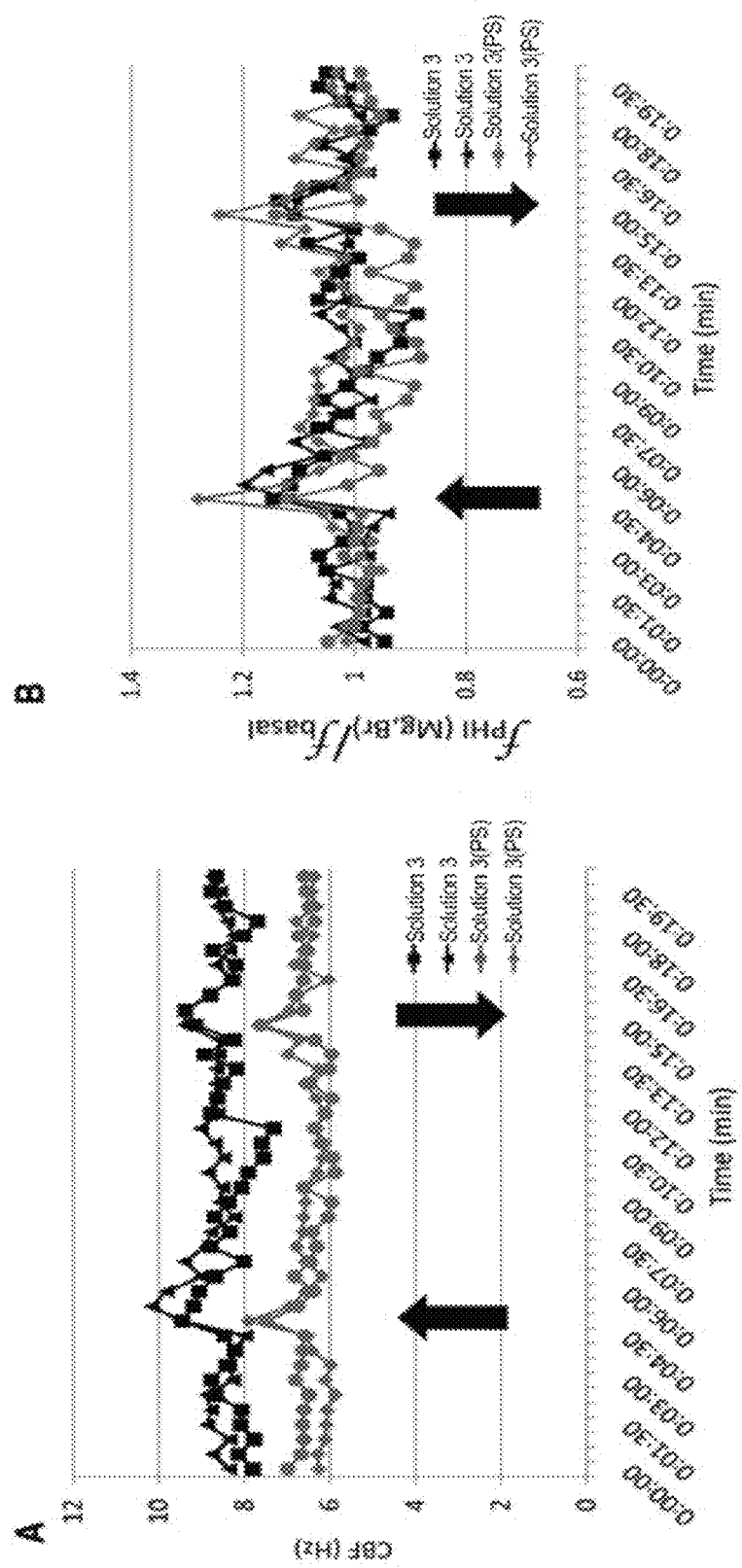
FIG. 14 is a series of images depicting that application of Solution 3 with or without preservative does not affect murine septal ciliary beat frequency. (A) continuous recording and analysis of ciliary beat frequency from murine nasal septal explants demonstrates that application of Solution 3 (0.075% potassium sorbate) (up arrow) does not alter ciliary beat frequency. Additionally, replacement of PHI with Locke Ringer's (down arrow) does not affect ciliary beat frequency. (B) normalization of ciliary beat frequency was performed to account for intrinsic differences in basal beat frequency of varying specimens. No alteration in $f_{PHI+MgBr}/f_{basal}$ is evident (tracing between up and down arrow).

(Winters S L, Davis C W, Boucher R C. Mechanosensitivity of mouse tracheal ciliary beat frequency: roles for Ca21, purinergic signaling, tonicity, and viscosity. Am J Physiol Lung Cell Mol Physiol. 2007; 292:L614-L624). Similar analysis was performed using Solution 3. As demonstrated in FIG. 14A, the addition of these elements had no detrimental effects on murine septal ciliary beat frequency.

Sinonasal Mucosal Regeneration

Figure 15:
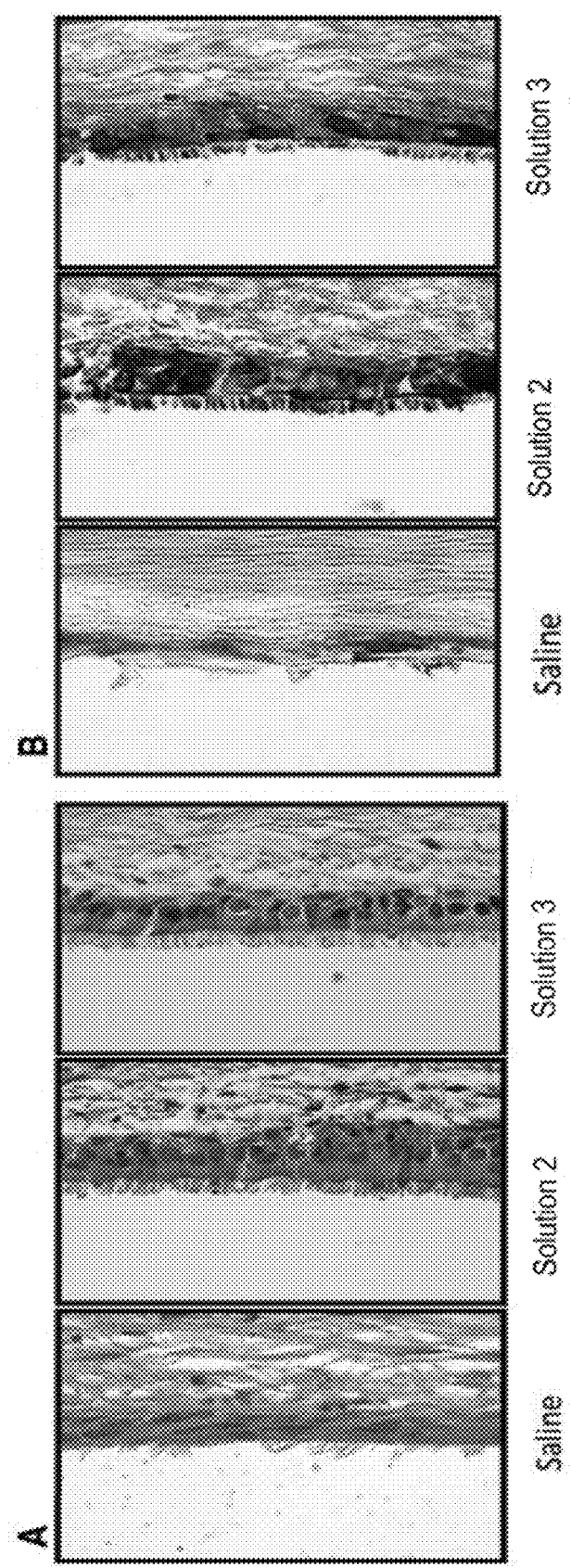
FIG. 15 is a series of images depicting Solution 2 and Solution 3 accelerate mucosal regeneration with ciliated epithelium. Representative sections through the injury site stained with (A) hematoxylin and eosin or (B) immunohistochemistry for the respiratory ciliary marker, type IV β-tubulin, demonstrate normal-appearing respiratory mucosa with a brush border in the treated sinuses compared with the saline sinuses.

Mucosal stripping of the medial wall of the rabbit maxillary sinus with subsequent daily topical treatments for 14 days was performed as described above. A total of 18 maxillary sinuses were analyzed. Representative photomicrographs of H&E-stained sections of saline-treated sinuses versus sinuses treated with Solution 2 or Solution 3 clearly demonstrate a profound effect of the solutions on mucosal regeneration (FIG. 15A). A similar effect of Solutions 2 and 3 on type IV β-tubulin immunohistochemistry is demonstrated in FIG. 15B.

Figure 16:
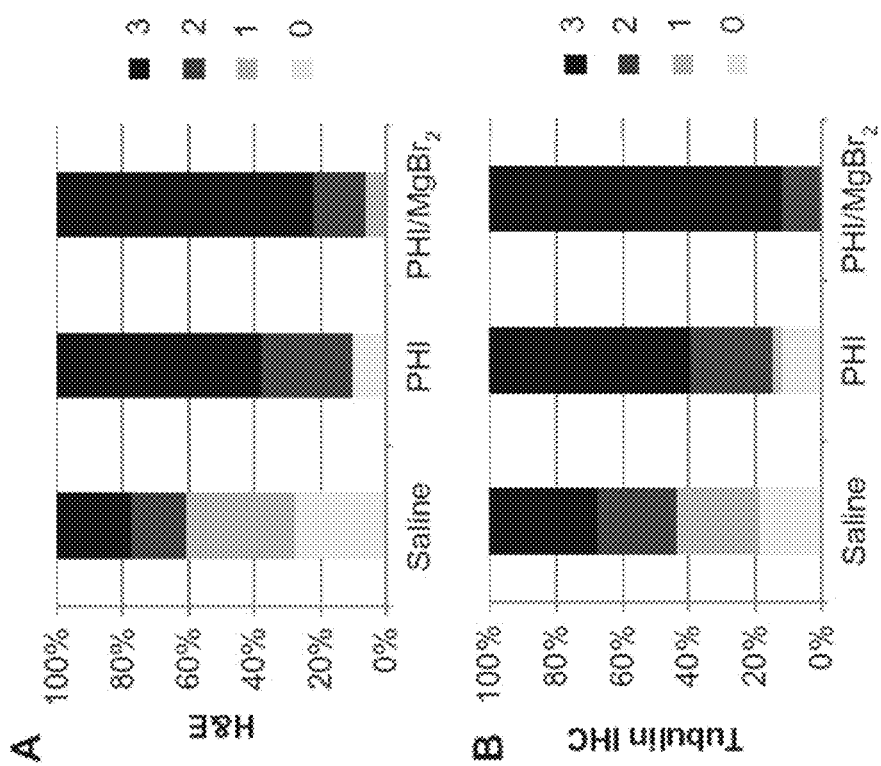
FIG. 16 is a series of graphs depicting the ciliation score by hematoxylin and eosin (H&E) and type IV β-tubulin immunohistochemistry analysis for saline, Solution 2, and Solution 3. The graphs show a breakdown of ciliation score as a percentage of total observations for each treatment by (A) H&E staining and (B) type IV β-tubulin immunohistochemistry.

Compiling all the data by frequency of distribution, Table 13 demonstrates significantly more scores of 3 in the sinuses treated with Solutions 2 and 3 as compared with those treated with saline as assessed by H&E staining as well as type IV β-tubulin immunohistochemistry ($P<0.01$). The median score for each treatment arm and analysis confirms this finding (Table 14). Furthermore, the percentage of the scoring breakdown for both outcome analyses illustrates the shift to near complete ciliation (score of 3) in the sinuses treated with Solutions 2 and 3 compared with the saline treated sinuses (FIG. 16).

any applicability in modulating the healing process of the respiratory mucosa following functional endoscopic sinus surgery.

Evaluation of the Solutions 2 and 3 with or without potassium sorbate as a preservative demonstrated no ciliotoxicity in the explant model. This is an important initial screening step in any potential sinonasal topical therapy, as very promising in vitro solutions have demonstrated significant ciliotoxicity. (Tamashiro E, Banks C A, Chen B, et al. In vivo effects of citric acid/zwitterionic surfactant cleansing solution on rabbit sinus mucosa. Am J Rhinol Allergy. 2009; 23:597-601). Furthermore, because preservatives added to nasal preparations have also demonstrated varying degrees of ciliotoxicity, the inventors screened the combinations of the solutions with or without the preservative potassium sorbate for potential synergistic ciliotoxicty. (Batts A H, Marriott C, Martin G P, et al. The effect of some preservatives used in nasal preparations on mucociliary clearance. J Pharm Pharmacol. 1989; 41:156-159).

To evaluate for mucosal regeneration, the inventors modified the previously reported rabbit maxillary sinus irrigation model to include a reproducible mucosal injury of the medial wall of the maxillary sinus. (Chiu A G, Antunes M B, Feldman M, et al. An animal model for the study of topical medications in sinusitis. Am J Rhinol 2007; 21:5-9). The data demonstrate that 2 weeks of treatment with daily irrigation of either Solution 2 or Solution 3 compared with saline statistically significant enhanced reciliation of the injury site. Thus, Solutions 2 and 3 hold tremendous promise as a postsurgical

TABLE 13

Frequency of Distribution and Percentage of Reciliation Score

| | | Reciliation Score | | | | |
| --- | --- | --- | --- | --- | --- | --- |
| | | 0 | 1 | 2 | 3 | Total |
| H&E | Saline | 20 (28) | 24 (33) | 12 (17) | 16 (22) | 72 (100) |
| | Solution 2 | 4 (10) | 0 (0) | 11 (28) | 25 (62) | 40 (100) |
| | Solution 3 | 0 (0) | 2 (6) | 5 (16) | 25 (78) | 32 (100) |
| Type IV β-tubulin staining | Saline | 14 (19) | 18 (25) | 17 (24) | 23 (32) | 72 (100) |
| | Solution 2 | 5 (12) | 1 (3) | 10 (25) | 24 (60) | 40 (100) |
| | Solution 3 | 0 (0) | 0 (0) | 4 (12) | 28 (88) | 32 (100) |

H&E, hematoxylin and eosin.
Values are frequency of distribution (percentage for each score as a function of the total observations).
A total of 72, 40, and 32 photomicrographs were analyzed for saline, Solution 2 and Solution 3, respectively for each evaluation of ciliation with distribution by grade for each treatment arm.

TABLE 14

Median Reciliation Score

| | Saline | Solution 2 | Solution 3 |
| --- | --- | --- | --- |
| H&E | 1 | 3 | 3 |
| β-tubulin IHC | 2 | 3 | 3 |

H&E hematoxylin and eosin; Enhanced reciliation following application of Solutions 2 and 3 is evident by the median score.

The mechanism of action of the cation-containing solutions presented herein appear to be aimed at modulating MMP activity, since the use of a cation-containing solution has previously been found to decrease expression of MMP messenger RNA while increasing the expression of TIMP RNA in cultured fibroblasts. (Pirayesh A, Dessy L A, Rogge F J, et al. The efficacy of a polyhydrated ionogen impregnated dressing in the treatment of recalcitrant diabetic foot ulcers: a multi-centre pilot study. Acta Chir Belg. 2007; 107:675-681). The inventors investigated whether Solutions 2 and 3 have irrigation, especially in cases where significant bone exposure (purposeful or inadvertent) is evident at the conclusion of the surgical procedure.

As shown in Table 15, below, treatment with either Solutions 2 or 3 had a significant effect on reciliation and healing in the sinonasal mucosa as compared to treatment with saline alone.

TABLE 15

| | H&E | Type IV β-Tubulin |
| --- | --- | --- |
| Saline (n = 9) | 1.33 | 1.68 |
| Solution 2 (n = 5) | 2.43 | 2.33 |
| Solution 3 (n = 4) | 2.72 | 2.88 |

EXAMPLE 4

The above prior safety studies demonstrated that the solution did not induce any ciliotoxicity. Additionally, as part of the safety study, a small pilot study was completed comparing Solutions 2 and 3 to saline on sinonasal mucosal healing. Following a 2-week trial with daily irrigation, the sinuses treated with Solutions 2 or 3 demonstrated significant improvement in mucosal regeneration compared to saline. Based on this pilot study, a new prospective randomized blinded animal study was designed to detect an effect size of 40%, with an 80% power and significance level of 5%.

Subjects and Methods

Power Calculation

Based on data from a previous study that demonstrated a significant improvement in paranasal mucosal reciliation following application of topical Solution 2 or Solution 3, a new prospective randomized blinded animal study was designed to detect an effect size of 40%, with an 80% power and significance level of 5%, using Epi Info, a Centers for Disease Control (CDC) statistical tool, a sample size of 24 rabbits was calculated. (DePoortere D, Kofonow J M, Chiu A G, et al. Enhanced post surgical remucosalization in a rabbit model. *Otolaryngol Head Neck Surg.* 2010; 143:P129).

Solutions

Solution 3 is a sterile isotonic formulation containing $K^+$, $Rb^+$, $Ca^{2+}$, $Zn^{2+}$, $Mg^{2+}$, $SO_4^{2-}$, and $Br^-$ without a preservative.

In Vivo Efficacy of Solution 3 to Accelerate Mucosal Healing

Prior to any animal experimentation approval was obtained from the Institutional Animal Care and Use Committee at the Philadelphia Veterans Affairs Medical Center (PVAMC). Twenty-four New Zealand white rabbits were used. Exposure of the maxillary sinus mucosa bilaterally was performed as previously described. (Chiu A G, Antunes M B, Palmer J N, et al. Evaluation of the in vivo efficacy of topical tobramycin against *Pseudomonas* sinonasal biofilms. *J Antimicrob Chemother.* 2007; 59:1130-1134; Bleier B S, Palmer J N, Gratton M A, et al. In vivo laser tissue welding in the rabbit maxillary sinus. *Am J Rhinol.* 2008; 22:625-628; Bleier B S, Palmer J N, Sparano A M, et al. Laser assisted cerebrospinal fluid leak repair: an animal model to test feasibility. *Otolaryngol Head Neck Surg.* 2007; 137:810-814).

Briefly, following a midline nasal dorsum skin incision, medially-based periosteal flaps were elevated bilaterally. The anterior face of the maxillary sinus was removed with an otologic drill (XPS-3000; Medtronic, Jacksonville, Fla.). Under microscopic visualization a 1-cm×1-cm mucosal flap was elevated off the medial wall of the maxillary sinus using otologic instruments and removed. Bilateral maxillary sinus indwelling irrigating catheters were then placed and secured as previously described. (Chiu A G, Antunes M B, Palmer J N, et al. Evaluation of the in vivo efficacy of topical tobramycin against *Pseudomonas* sinonasal biofilms. J Antimicrob Chemother. 2007; 59:1130-1134; Tamashiro E, Banks C A, Chen B, Gudis D A, Doghramji L, Myntti M, Chiu A G, Cohen N A. In vivo effects of citric acid/zwitterionic surfactant (CAZS) cleansing solution on rabbit sinus mucosa. *Am J Rhinol Allergy.* 2009; 23:597-601). Approximately 1.0 cm of tubing was placed into the sinus and the remainder was tunneled under the skin of the forehead, and brought out through a stab incision at the vertex of the cranium between the ears. Along the course of the catheter, vicryl sutures were used to drape the periosteum over the catheter. The hub of the tubing was capped and secured to the skin with a purse string suture of 3-0 nylon and the midline incision was closed with a running 3-0 nylon. Patency of the catheter was checked by instilling 3 cc of normal saline (NS) or Solution 3 and confirming drainage through the ipsilateral nares. Randomization of sinus was performed prior to instillation of any solution. For each rabbit, 1 side received NS while the other side received Solution 3. Thus, each rabbit served as its own "saline" control, while the sides were randomized. Each sinus was irrigated daily with 3 cc of solution for 14 days. At the completion of the therapeutic trial, rabbits were euthanized using sedation and an intracardiac barbiturate overdose.

Snouts were harvested, fixed for 24 hours in 10% normal buffered formalin, and then decalcified for 48 hours in rapid decalcifier (Electron Microscopy Sciences, Hatfield, Pa.). After sectioning, dehydrating, and paraffin embedding, the tissue was sectioned and remucosalization with ciliated cells was assessed at the site of injury by hematoxylin and eosin (H&E) staining as well as immunohistochemistry (IHC) for type IV β-tubulin, a marker of motile cilia.

The stripping was performed in the middle third of the medial wall of the maxillary sinuses, 4 representative segments of regenerated mucosa were imaged at ×40 magnification from each side. The micrographs from both H&E and IHC staining were assembled in random order and reviewed by 2 blinded trained observers. A semi quantitative grading of reciliation was used based on the amount of mucosa covered with cilia (0=no cilia; 1=<30% cilia; 2=31-60% cilia; 3=>60% cilia) as previously described. (DePoortere D, Kofonow J M, Chiu A G, et al. Enhanced post surgical remucosalization in a rabbit model. *Otolaryngol Head Neck Surg.* 2010; 143:P129).

A chi-square test was used to compare the distributions in each group and determine significance.

Results

Figure 17:
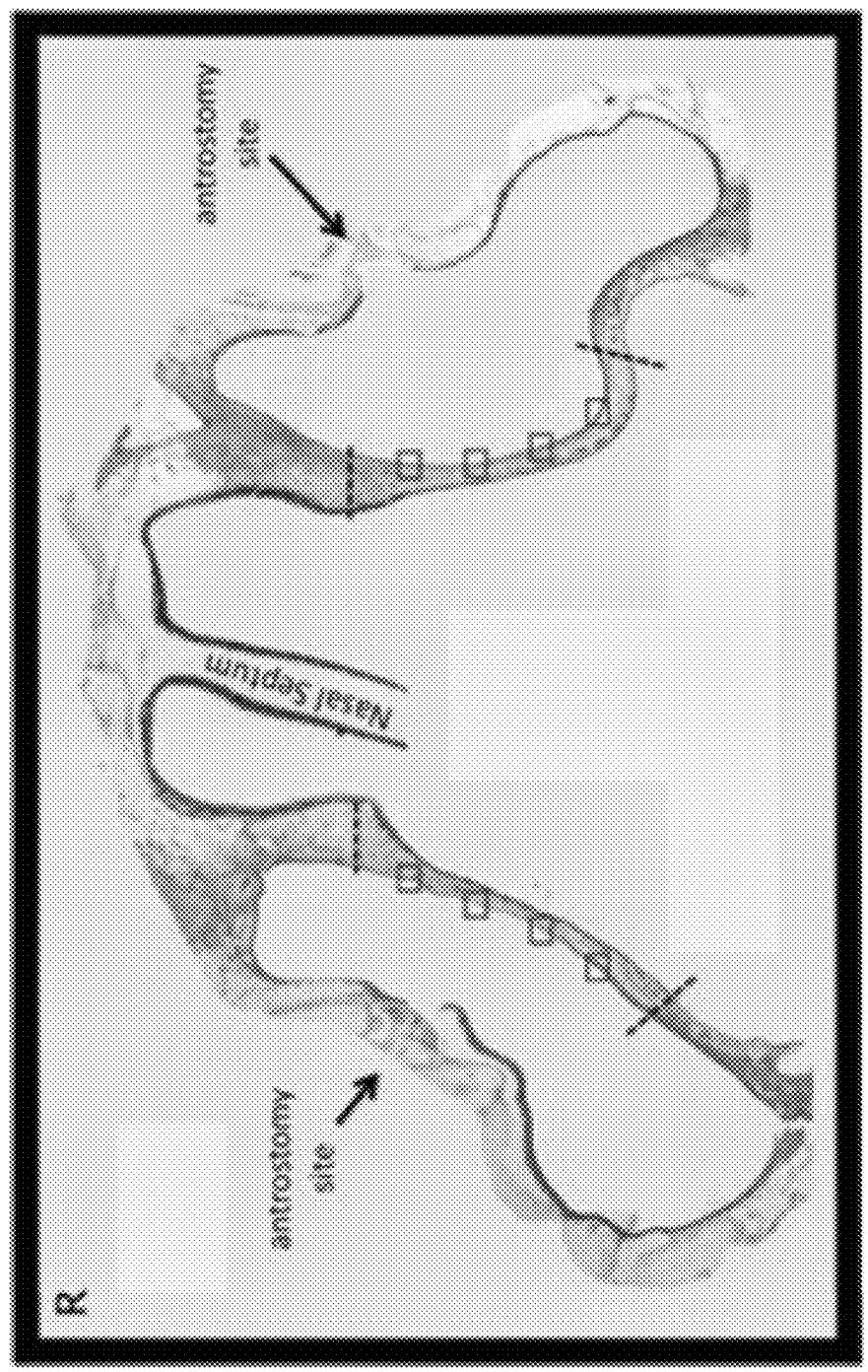
FIG. 17 is an image of a rabbit snout following mucosal stripping and subsequent healing. A montage of multiple images reconstructing a rabbit snout following surgery and treatment. Arrows illustrate the surgical antrostomy created to access the sinus, and through which the irrigating catheter was placed. Dashed lines represent the approximate superior and inferior margin of the mucosal injury while the boxes represent the distribution of photomicrographs obtained for analysis.

To illustrate the experimental paradigm, a montage of a rabbit snout was assembled demonstrating the surgical antrostomy locations, region along the medial wall of mucosal stripping, as well as the approximate regions of the 4 random photomicrographs obtained for evaluation (FIG. 17).

Figures 18A, 18B:
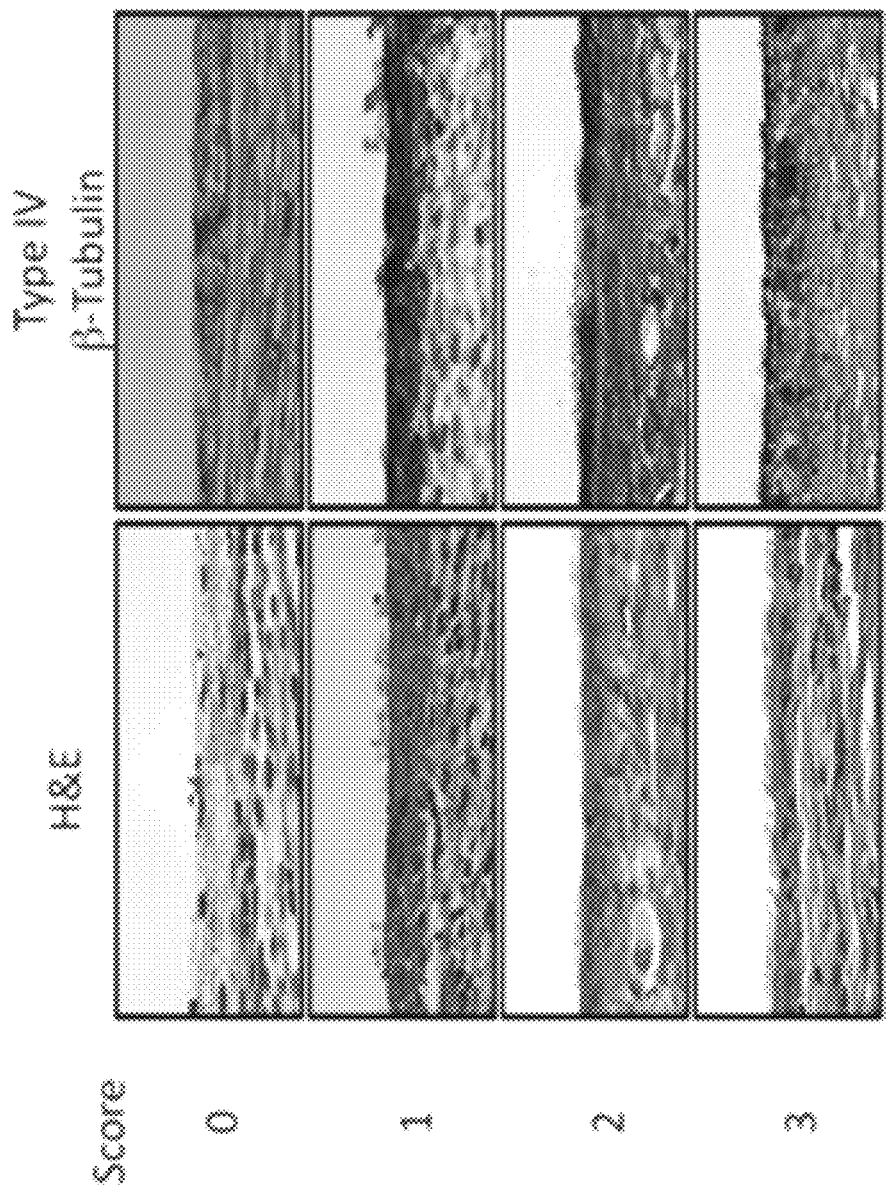
FIG. 18 is a series of images depicting a semi quantitative grading of reciliation. (A) sections of rabbit snout fixed and stained with hematoxylin and eosin; (B) sections of rabbit snout fixed and subjected to immunohistochemistry for type IV β-tubulin, a marker of respiratory cilia. 0=no cilia; 1=less than 30% cilia; 2=30%-60% cilia; 3=>60% cilia.

The degree of mucosal regeneration was scored as described above with representative photomicrographs of each grade by H&E staining and type IV β-tubulin IHC displayed in FIG. 18.

Mucosal stripping of the medial wall of the rabbit maxillary sinus with subsequent daily topical treatments for 14 days was performed as described above. A total of 48 maxillary sinuses were analyzed with 4 photomicrographs of each sinus obtained yielding a total of 192 images. Representative photomicrographs of H&E stained sections (FIG. 19A) as well as type IV tubulin immunohistochemistry (FIG. 19B) of saline treated vs. Solution 3-treated sinuses clearly demonstrate a profound effect of Solution 3 on mucosal regeneration. The Solution 3-treated sinuses demonstrate normal appearing respiratory mucosa with an intact brush border compared to the saline-treated sinuses demonstrating sparse ciliation and flattened fibroblastic appearing cells.

Figures 19A, 19B:
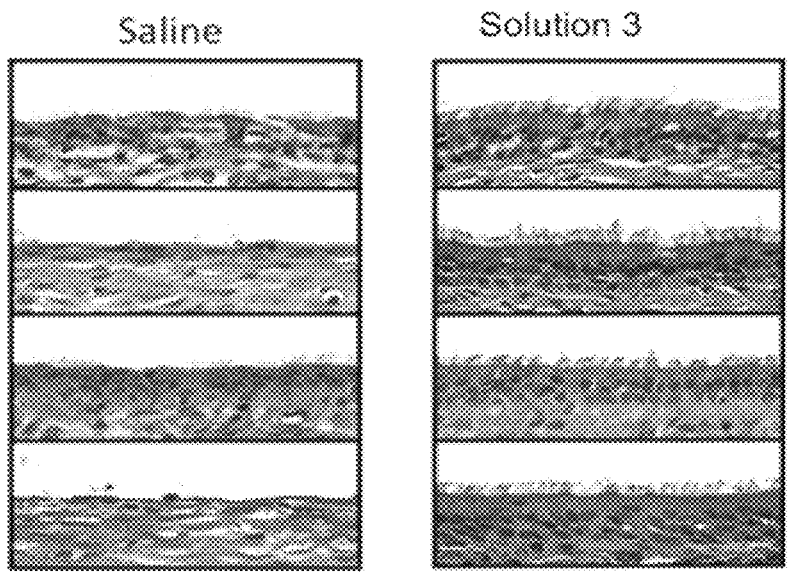
FIG. 19 is a series of images depicting that the application of Solution 3 accelerates mucosal regeneration with ciliated epithelium. Representative sections through the injury site stained with (A) hematoxylin and eosin or (B) immunohistochemistry for the respiratory ciliary marker, type IV β-tubulin demonstrate normal-appearing respiratory mucosa with a brush border in the treated sinuses compared to the saline treated sinuses with sparse ciliation and flattened fibroblastic-appearing cells.

A frequency of distribution table for all 192 images demonstrates a profound shift toward complete reciliation in Solution 3 (Table 16). H&E staining comparison demonstrated NS-treated sinuses (n=24) had substantial bare areas with predominant ciliation scores under 33%, only 93 images of 192 (48.43%) were scored above 66%. The Solution 3-treated group (n=24) achieved a statistically significant improve in ciliary density, 175 pictures out of 192 (91.14%) were scored above 66%, chi-square value of 147.25 (p<0.01) (FIG. 19A). These results were confirmed with a cilia specific IHC staining for Type IV β-tubulin, where the frequency distribution again evinced significant lower ciliation in the NS-treated group when compared with the Solution 3-treated sinuses, chi-square 147.73 (p<0.01) (FIG. 19B). The median score for the Solution 3-treated sinuses was 3 for both H&E and type IV β-tubulin IHC compared to 1 for both analyses of the saline-treated (p<0.01).

Additionally, the initial data illustrated the efficacy of Solution 2 in accelerating the sinonasal mucosal healing process. An effect size of 40%, with an 80% power and significance level of 5% was used for detection. Utilizing 24 rabbits, and based on our semi-quantitative scoring system for ciliated mucosal regeneration, the inventors demonstrate a robust difference in sinonasal wound healing, including debridement of damaged tissue, following a 2-week course of daily sinus irrigation with Solution 3 as compared to NS. It is important to note that this model does not take into account infection, or pre-existing inflammation as is often encountered in CRS patients undergoing surgical intervention.

TABLE 16

Frequency and Distribution of Scores for H&E and Immunohistochemistry for Both Treatments for all Rabbits

|  | 0% | <30% | 30%-60% | >60% |
|---|---|---|---|---|
| H&E |  |  |  |  |
| Saline | 53 | 46 | 31 | 62 |
| Solution 3 | 3 | 2 | 12 | 175 |
| Tubulin |  |  |  |  |
| Saline | 53 | 46 | 18 | 75 |
| Solution 3 | 3 | 1 | 2 | 186 |

*A total of 192 photomicrographs were analyzed for each evaluation of ciliation with distribution by grade for each treatment arm.
H&E = hematoxylin and eosin;

EXAMPLE 6

Materials and Methods

Solutions

For these experiments, Solutions 3 and 4 were compared to saline in a rabbit model for sinonasal mucosal injury. Solution 3 is a sterile isotonic formulation containing $K^+$, $Kb^+$, $Ca^{2+}$, $Zn^{2+}$, $Mg^{2+}$, $SO_4^{2-}$, and $Br^-$ without a preservative. Solution 4 is a sterile isotonic formulation containing $Mg^{2+}$, $Br^-$, Na+, Cl−, and $SO_4^{2-}$ without a preservative.

Prior to any animal experimentation approval was obtained from the Institutional Animal Care and Use Committee at the Philadelphia Veterans Affairs Medical Center (PVAMC). Six New Zealand white rabbits were used. Exposure of the maxillary sinus mucosa bilaterally was performed as previously described. (Chiu A G, Antunes M B, Palmer J N, et al. Evaluation of the in vivo efficacy of topical tobramycin against *Pseudomonas* sinonasal biofilms. *J Antimicrob Chemother.* 2007; 59:1130-1134; Bleier B S, Palmer J N, Gratton M A, et al. In vivo laser tissue welding in the rabbit maxillary sinus. *Am J Rhinol.* 2008; 22:625-628; Bleier B S, Palmer J N, Sparano A M, et al. Laser assisted cerebrospinal fluid leak repair: an animal model to test feasibility. *Otolaryngol Head Neck Surg.* 2007; 137:810-814).

Briefly, following a midline nasal dorsum skin incision, medially-based periosteal flaps were elevated bilaterally. The anterior face of the maxillary sinus was removed with an otologic drill (XPS-3000; Medtronic, Jacksonville, Fla.). Under microscopic visualization a 1-cm×1-cm mucosal flap was elevated off the medial wall of the maxillary sinus using otologic instruments and removed. Bilateral maxillary sinus indwelling irrigating catheters were then placed and secured as previously described. (Chiu A G, Antunes M B, Palmer J N, et al. Evaluation of the in vivo efficacy of topical tobramycin against *Pseudomonas* sinonasal biofilms. *J Antimicrob Chemother.* 2007; 59:1130-1134; Tamashiro E, Banks C A, Chen B, Gudis D A, Doghramji L, Myntti M, Chiu A G, Cohen N A. In vivo effects of citric acid/zwitterionic surfactant (CAZS) cleansing solution on rabbit sinus mucosa. *Am J Rhinol Allergy.* 2009; 23:597-601). Approximately 1.0 cm of tubing was placed into the sinus and the remainder was tunneled under the skin of the forehead, and brought out through a stab incision at the vertex of the cranium between the ears. Along the course of the catheter, vicryl sutures were used to drape the periosteum over the catheter. The hub of the tubing was capped and secured to the skin with a purse string suture of 3-0 nylon and the midline incision was closed with a running 3-0 nylon. Patency of the catheter was checked by instilling 3 cc of normal saline (NS) or Solution 3 or 4 and confirming drainage through the ipsilateral nares. Randomization of sinus was performed prior to instillation of any solution. For each rabbit, 1 side received NS while the other side received either Solution 3 or Solution 4. Thus, each rabbit served as its own "saline" control, while the sides were randomized. Each sinus was irrigated daily with 3 cc of solution for 14 days. At the completion of the therapeutic trial, rabbits were euthanized using sedation and an intracardiac barbiturate overdose.

One of the six rabbits had no first surgery due to neurological issues but was used as a time 0 for stripping. The remaining 5 rabbits, illustrating 10 sinuses, were used to demonstrate the efficacy of Solution 3 versus Solution 4 with saline used as a control. The saline control was administered to 2 sinuses; Solution 3 was administered to 3 sinuses; and Solution 4 was administered to 5 sinuses.

Snouts were harvested, fixed for 24 hours in 10% normal buffered formalin, and then decalcified for 48 hours in rapid decalcifier (Electron Microscopy Sciences, Hatfield, Pa.). After sectioning, dehydrating, and paraffin embedding, the tissue was sectioned and remucosalization with ciliated cells was assessed at the site of injury by hematoxylin and eosin (H&E) staining.

The stripping was performed in the middle third of the medial wall of the maxillary sinuses, 4 representative segments of regenerated mucosa were imaged at ×40 magnification from each side. The micrographs from H&E staining were assembled in random order and reviewed by 2 blinded trained observers. A semi quantitative grading of reciliation was used based on the amount of mucosa covered with cilia (0=no cilia; 1=<30% cilia; 2=31-60% cilia; 3=>60% cilia) as previously described. (DePoortere D, Kofonow J M, Chiu A G, et al. Enhanced post surgical remucosalization in a rabbit model. *Otolaryngol Head Neck Surg.* 2010; 143:P129).

A chi-square test was used to compare the distributions in each group and determine significance.

Results

Figure 20:
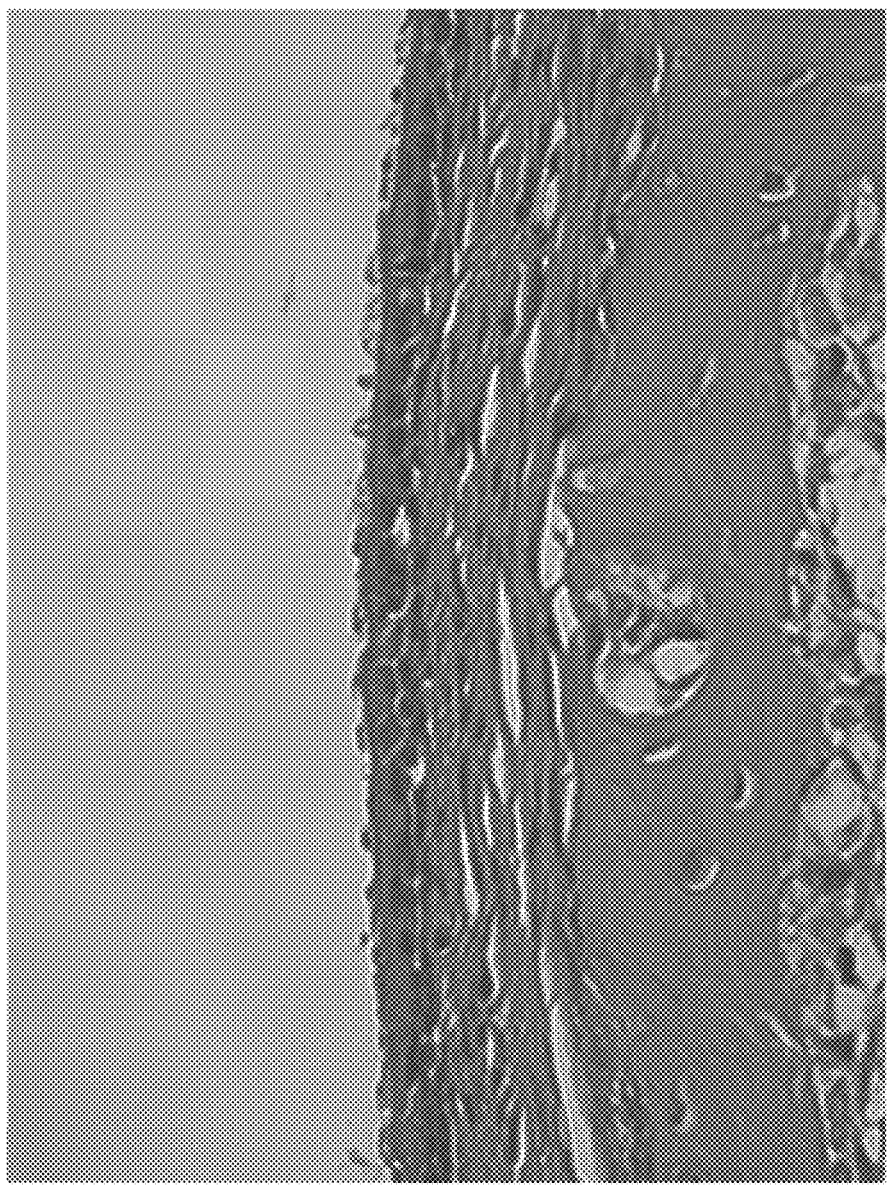
FIG. 20 is an image depicting a representative section through the injury site demonstrating the respiratory mucosa after treatment with saline.

Representative photomicrographs of H&E stained sections of saline treated (FIG. 20) vs. Solution 3-treated sinuses (FIG. 21) vs. Solution 4-treated sinuses (FIG. 22) clearly demonstrate a profound effect of Solutions 3 and 4 on mucosal regeneration. The Solution 3-treated and Solution 4-treated sinuses demonstrate normal appearing respiratory mucosa with an intact brush border compared to the saline-treated sinuses demonstrating sparse ciliation and flattened fibroblastic appearing cells.

TABLE 17

|  | H&E |
|---|---|
| Saline (n = 2) | 1.42 |
| Solution 4 (n = 5) | 2.73 |
| Solution 3 (n = 3) | 2.94 |

In comparing the results in Table 17 to the results in Table 15, there seems to be at least an additive effect, if not a synergistic effect, of the addition of the $Mg^{2+}$, $Br^-$ and possibly the $Na^+$, $Cl^-$, and $SO_4^{2-}$ ions in Solution 3 (containing $K^+$, $Rb^+$, $Ca^{2+}$, $Zn^{2+}$, $Na^+$, $Cl^+$, and $SO_4^{2-}$, $Mg^{2+}$, and $Br^-$) as compared to Solution 2 containing only $K^+$, $Rb^+$, $Ca^{2+}$, and $Zn^{2+}$.

Figure 21:
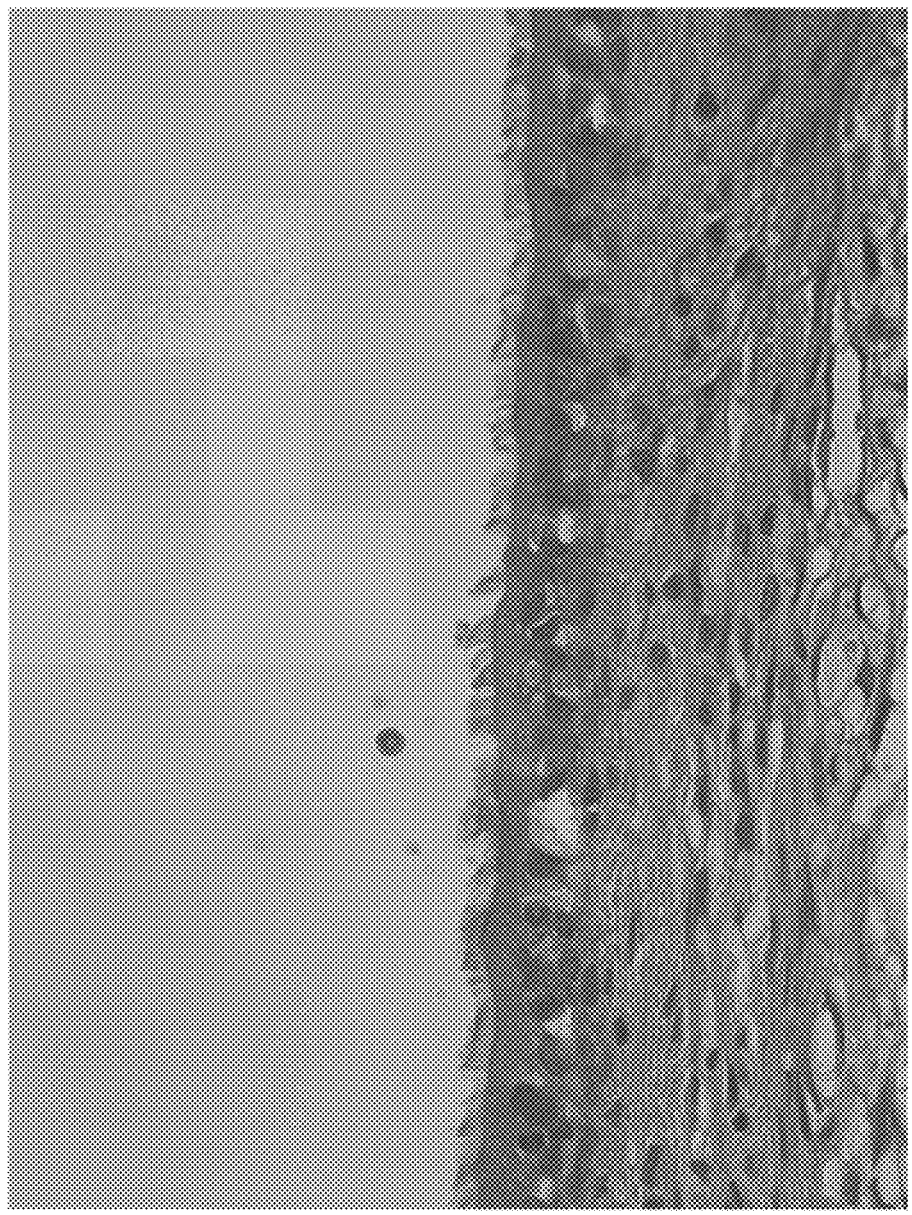
FIG. 21 is an image depicting a representative section through the injury site demonstrating the respiratory mucosa after treatment with Solution 3 (sterile isotonic formulation containing $K^+$, $Rb^+$, $Ca^{2+}$, $Zn^{2+}$, $Mg^{2+}$, and $Br^-$ without the preservative potassium sorbate).
Figure 22:
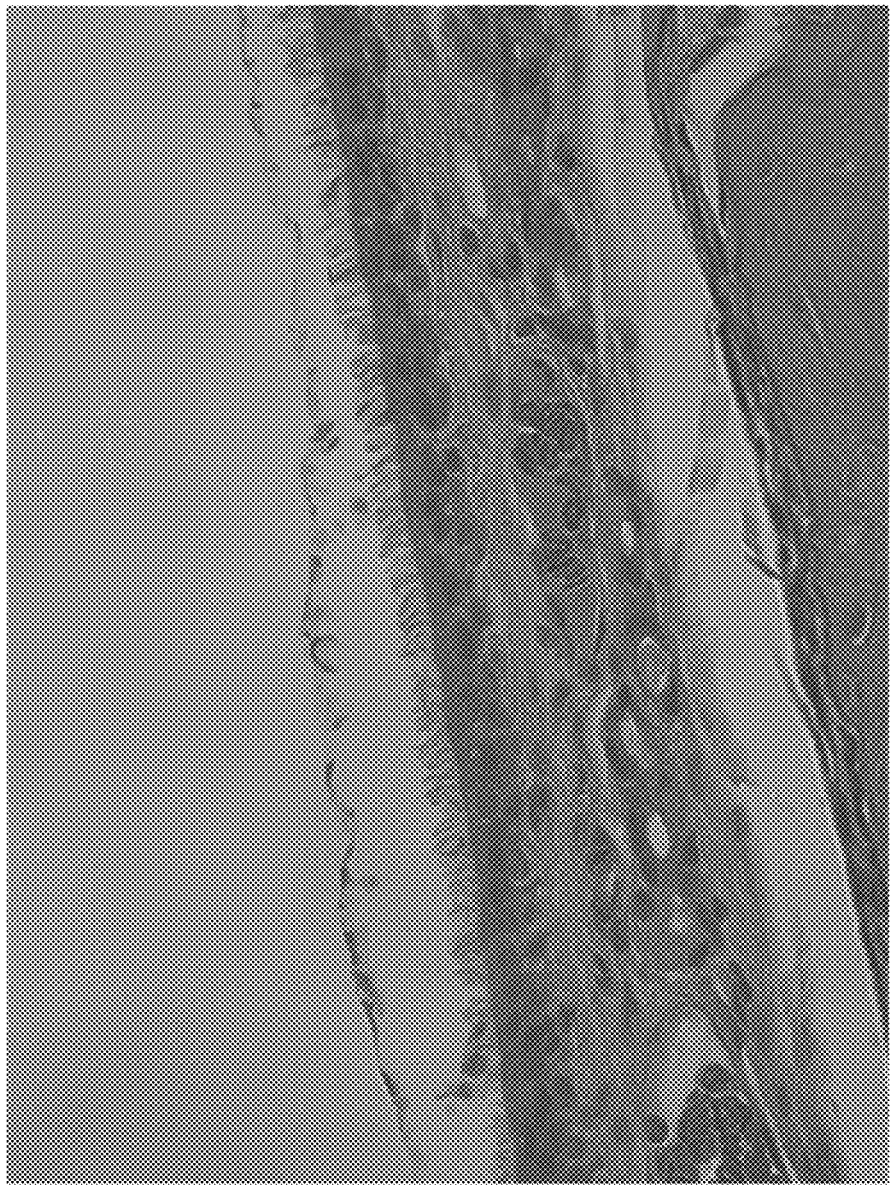
FIG. 22 is an image depicting a representative section through the injury site demonstrating the respiratory mucosa after treatment with Solution 4 (sterile isotonic formulation containing $Mg^{2+}$, $Br^-$, Na+, Cl-, and $SO_4^{2-}$ without the preservative potassium sorbate).

Unexpectedly, Solution 4 containing only $Mg^{2+}$, $Br^-$, $Na^+$, $Cl^-$, and $SO_4^-$ ions seemed to perform at least as well as if not even better than Solution 2. These results seem to indicate that Solutions 3 and 4 have potential to be used for promoting sinus wound healing, including debridement of damaged tissue, after sinus surgery as illustrated in FIGS. 21 and 22. In addition, both solutions demonstrated enhanced ciliated remucosalization as also illustrated in FIGS. 21 and 22.

CONCLUSION

Advances in surgical instrumentation have improved the rhinologist's ability to practice mucosal preservation surgery. It is well accepted that mucosal stripping leads to poor healing of the respiratory mucosa with loss of ciliary function in critical areas resulting in adverse clinical outcomes. However, inadvertent mucosal stripping does occur as well as clinical situations dictating intentional mucosal resection. Solutions 3 and 4 were shown to be capable of debriding damaged tissue to enhance wound healing as well as enhance mucosal reciliation in the sinonasal mucosa. In the rabbit model, daily irrigation with Solutions 2, 3, or 4 enhanced ciliated remucosalization compared to saline, thus illustrating these solutions have applicability in promoting sinus wound healing after sinus surgery.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of promoting mucosal reciliation in a subject comprising:
   administering an effective amount of a sterile isotonic solution to a subject in need thereof comprising:
      a therapeutically effective amount of potassium ions;
      a therapeutically effective amount of rubidium ions;
      a therapeutically effective amount of calcium ions;
      a therapeutically effective amount of zinc ions;
      a therapeutically effective amount of magnesium ions;
      a therapeutically effective amount of bromide ions;
      a therapeutically effective amount of sulfate ions;
      a therapeutically effective amount of citric acid; and
      a pharmaceutically acceptable carrier;
   wherein the sterile isotonic solution has no sodium ions and
   wherein the administration of the isotonic solution causes mucosal reciliation.

2. The method of claim 1, wherein the isotonic solution is administered at least once daily.

3. The method of claim 1, wherein the isotonic solution is administered to the subject for at least 14 days.

4. The method of claim 1, wherein tonicity of the solution is 0.9%.

5. The method of claim 1, wherein the pharmaceutically acceptable carrier is water.

6. The method of claim 1, wherein the amount of potassium ions is between about 0.02% to about 3.0% (w/v).

7. The method of claim 1, wherein the amount of rubidium ions is between about 0.0001% to about 4.0% (w/v).

8. The method of claim 1, wherein the amount of calcium ions is between about 0.0000055 to about 1.3% (w/v).

9. The method of claim 1, wherein the amount of zinc ions is between about 0.0000057% to about 2.12% (w/v).

10. The method of claim 1, wherein the amount of magnesium ions is between about 0.0075 to about 1.14% (w/v).

11. The method of claim 1, wherein the amount of bromide ions is between about 0.0002% to about 2.6% (w/v).

12. The method of claim 1, wherein the amount of sulfate ions is between about 0.000078% to about 4.5% w/v.

13. The method of claim 1, wherein the amount of potassium ions is about 0.41% w/v.

14. The method of claim 1, wherein the amount of rubidium ions is about 0.0031% w/v.

15. The method of claim 1, wherein the amount of calcium ions is about 0.00011% w/v.

16. The method of claim 1, wherein the amount of zinc ions is about 0.000024% w/v.

17. The method of claim 1, wherein the amount of magnesium ions is about 0.14% w/v.

18. The method of claim 1, wherein the amount of bromide ions is about 0.0044% w/v.

19. The method of claim 1, wherein the amount of sulfate ions is about 0.0015% w/v.

* * * * *